United States Patent [19]

Kutyavin et al.

[11] Patent Number: 5,912,340
[45] Date of Patent: Jun. 15, 1999

[54] SELECTIVE BINDING COMPLEMENTARY OLIGONUCLEOTIDES

[75] Inventors: Igor V. Kutyavin, Bothell; Jinsuk Woo, Lynnwoode; Eugeny A. Lukhtanov; Rich B. Meyer, Jr., both of Bothell; Howard B. Gamper, Woodinville, all of Wash.

[73] Assignee: Epoch Pharmaceuticals, Inc., Bothell, Wash.

[21] Appl. No.: 08/539,097

[22] Filed: Oct. 4, 1995

[51] Int. Cl.$^6$ .................................................... C07H 21/04
[52] U.S. Cl. ........................ 536/24.5; 536/26.6; 536/24.3
[58] Field of Search ................. 536/24.5, 26.6, 536/24.3

[56] References Cited

FOREIGN PATENT DOCUMENTS

| WO93/03736 | 3/1993 | WIPO | ............................ A61K 31/70 |
| 95/05391 | 2/1995 | WIPO . | |
| 95/14707 | 6/1995 | WIPO | ............................ C07H 19/16 |

OTHER PUBLICATIONS

Scheit et al. Studia Biophysica vol. 55, No. 1, 1976. pp. 21–27.
Inoue et al. Chemical Abstracts vol. 108, No. 21, 1988. p. 752, col. 1.
Database WPI, AN 87–352165[50] (see abstract) & Patent Abstracts of Japan, vol. 012, No. 139 (see abstract).
Case–Green et al. Nucleic Acids Research, vol. 22, No. 2, 1994. pp. 131–136.
Martin et al. Nucleic Acids Research, vol. 13, No. 24, 1985. pp. 8927–8938.
Chollet et al. Nucleic Acids Research, vol. 16, No. 1, 1988. pp. 305–317.
Kuimelis et al. Nucleic Acids Research, vol. 22, No. 8, 1994. pp. 1429–1436.
Ishikawa et al. Chemical Abstracts, vol. 116, No. 13, 1992. pp. 949. col. 2.
Newman et al. Biochemistry, vol. 29, No. 42, 1990. pp. 9891–9901.
Richardson et al. Journal of the American Chemical Society, vol. 113, No. 13, 1991. pp. 5109–5111.
Woo J et al. Nucleic Acids Research, vol. 24, No. 13, 1996. pp. 2470–2475.2.
Strobel, S.A., et al. (1991) *Science*, 254:1639.
Weinstock, P., et al. (1990) *Nucl. Acids Res.*, 18:4207.
Roca, A.I., et al. (1990) *Rev. Biochem. Mol. Biol.*, 25:415.
Robins et al.(1982) *Can. J. Chem.*, 60:554.
Robins et al.(1983) *J. Org. Chem.*, 48:1854.
Meyer, et al., (1989) *J. Am. Chem. Soc.*, 111:8517.
Kobayashi (1973) *Chem. Phar. Bull.*, 21:941–951.
Sonveaux (1986) Bioorganic Chemistry, 14:274–325.
Jones (1984) "Oligonucleotide Synthesis, a Practical Approach", M.J. Gait, Ed., IRL Press, P23–34.
Langer et al. (1981) *Proc. Natl. Acad. Sci. USA*, 78:6633–6637. "Nucleic Acid Hybridisation, a Practical Approach", Hames and Higgins, Eds., IRL Press, 1985.
Gall and Pardue, (1969) *Proc. Natl. Acad. Sci., U.S.A.*, 63:378–383.
John et al., (1969) Nature, 223:582–587.
"Physical Biochemistry", Freifelder, D., W.H. Freeman & Co., 1982, pp. 537–542.
Tijssen, P., (1985) "Practice and theory of Enzyme Immunoassays, Laboratory Techniques in Biochemistry and Molecular Biology", Burdon, R.H., van Knippenberg, P.H., Eds, Elsevier, pp. 9–20.
Connolly, et al., (1989) *Nucleic Acids Res.*,17:4957–4974.
Fathi, et al. (1990) *Tetrahedron Lett.*, 31:319–322.
Sinha, et al. (1984) Nucleic Acids Research, 12:4539.
Alul, et al. (1991) *Nucleic Acids Res.*, 19:1527–1532.
Atkinson, T. and Smith, M. (1984) "Oligonucleotide Synthesis, a Practical Approach", M. Gait, Ed., IRL Press, Washington, D.C., pp. 35–81.

*Primary Examiner*—Scott W. Houtteman
*Attorney, Agent, or Firm*—Klein & Szekeres, LLP

[57] ABSTRACT

In a matched pair of oligonucleotides (ODNS) each member of the pair is complementary or substantially complementary in the Watson Crick sense to a target sequence of duplex nucleic acid where the two strands of the target sequence are themselves complementary to one another. The ODNs include modified bases of such nature that the modified base forms a stable hydrogen bonded base pair with the natural partner base, but does not form a stable hydrogen bonded base pair with its modified partner. This is accomplished when in a hybridized structure the modified base is capable of forming two or more hydrogen bonds with its natural complementary base, but only one hydrogen bond with its modified partner. Due to the lack of stable hydrogen bonding with each other, the matched pair of oligonucleotides have a melting temperature under physiological or substantially physiological conditions of approximately 40° C. or less. However each of the matched ODN pair of the invention forms a substantially stable hybrid with the target sequence in each strand of the duplex nucleic acid. The hybrids of target duplex nucleic acids formed with the ODN pairs of the invention are useful for gene mapping and in diagnostic and therapeutic applications.

26 Claims, No Drawings

SELECTIVE BINDING COMPLEMENTARY OLIGONUCLEOTIDES

BACKGROUND OF THE INVENTION

1. Field of the Invention

The present invention is directed to oligonucleotides which include modified bases-such that members of a matched pair of the oligonucleotides are unable to form stable hybrids with one another and yet are able to form stable, sequence specific hybrids with complementary unmodified DNA or RNA strands. The present invention is also directed to the use of such oligonucleotides as an anti-sense and anti-gene agents and probes for specific sequences in single or double stranded DNA or RNA.

2. Brief Description of Prior Art

It is well known that oligonucleotides (ODNs) do not readily hybridize to complementary sequences in double stranded DNA or in DNA or RNA secondary structure. Nevertheless, it is also known that the ability to sequence specifically access double stranded DNA or single stranded RNA or DNA in secondary structure would have great utility in gene mapping, diagnostics and therapeutic applications. Methods known in the prior art which, although limited in scope, accomplish hybridization of ODNs to duplex nucleic acids include triplex formation (see Troel. S. et al. Science 1991, 254, 1639), the branch capture reaction (Weinstock, P. et al. Nucl. Acids Res. 1990, 18, 4207), recombinase mediated synapsis (Roca, A. I.; et al. Rev. Biochem. Mol. Biol. 1990, 25, 415) and cross-linking of the hybridized ODN to at least one strand of the duplex nucleic acid (PCT application WO 93/03736, published Mar. 4, 1993).

There is however still a significant need, and room for improvement in the art, for oligonucleotides which are able to sequence specifically hybridize to duplex nucleic acids. The present invention provides such oligonucleotides.

SUMMARY OF THE INVENTION

In accordance with the present invention a matched pair of oligonucleotides (ODNs) are provided where each member of the pair is complementary or substantially complementary in the Watson Crick sense to a target duplex sequence. However the ODNs include modified bases of such nature that the modified base forms stable hydrogen bonded base pairs with the natural partner base, but does not form stable hydrogen bonded base pairs with its modified partner. Generally speaking, this is accomplished when in a hybridized structure the modified base is capable of forming two or more hydrogen bonds with its natural complementary base, but only one or no hydrogen bonds with its modified partner. Thus, the matched pair of oligonucleotides in accordance with the present invention do not form substantially stable hydrogen bonded hybrids with one another, as manifested in a melting temperature (under physiological or substantially physiological conditions) of approximately 40° C. or less. The ODNS of the invention, however, form substantially stable hybrids with the target sequence in each strand of duplex nucleic acid. Due to the increased (approximately double) number of hydrogen bonds in such hybrids (when compared to hybrids that would be formed between a single ODN and duplex nucleic acid) the hybrids formed with the ODN pairs of the present invention are more stable, and lend themselves for gene mapping, diagnostic and therapeutic use. The ODNs of the present invention are termed Selective Binding Complementary (SBC) ODNs, and may be referred to under that name in this application for patent.

The SBC ODNs of the present invention may optionally be connected to one another with a covalent "tether" of such nature that the tether does not prevent hybridization of each ODN to one strand of the target sequence. The SBC ODNs of the present invention may optionally include modifications in the sugar moiety, in the phosphate backbone, and may have cross-linking groups and/or reporter groups attached.

DETAILED DESCRIPTION OF THE INVENTION

As is noted in the Summary of the present application, a key feature of the SBC ODNs of the present invention is that each one of a matched pair of the SBC ODNs is complementary, or substantially complementary, to one target sequence in duplex nucleic acid wherein the target sequences are themselves complementary or substantially complementary to one another, and each one of the matched pair of SBC ODNs forms a stable hydrogen bonded hybrid with one strand of the target sequence. Due to the presence of modified bases in the SBC ODN, although these ODNs are complementary to one another, they are unable to form a stable hydrogen bonded hybrid, as manifested by a melting temperature of approximately 40° C. or less. Thus, the SBC ODNs are not hybridized to one another but they readily hybridize, especially in the presence of recombinase enzymes when the target is in long double stranded DNA, with both strands of the target sequence.

In accordance with well established convention in the art, the naturally occurring nucleotide components of nucleic acids have the designation A, U, G and C, (RNA) and dA, dT, dG and dC (DNA). As it will become apparent from the following description, the present invention applies to both ribonucleotides and deoxyribonucleotides, and therefore, unless the context otherwise requires, no distinction needs to be made in this description between A and dA, U and dT, etc.

Analogs of A which are modified in the base portion to form in an ODN-to-nucleic acid or ODN-to-ODN interaction a stable hydrogen bonded pair with T, (or U in the case of RNA) but not with T' are designated A'. Analogs of T which are modified in the base portion to form in an ODN-to-nucleic acid or ODN-to-ODN interaction a stable hydrogen bonded pair with A, but not with A' are designated T'. Analogs of G which are modified in the base portion to form in an ODN-to-nucleic acid or ODN-to-ODN interaction a stable hydrogen bonded pair with C, but not with C' are designated G'. Analogs of C which are modified in the base portion to form in an ODN-to-nucleic acid or ODN-to-ODN interaction a stable hydrogen bonded pair with G, but not with G' are designated C'. The foregoing conditions are satisfied when each of the A', T', G' and C' nucleotides (collectively the modified SBC nucleotides) form, in an ODN-to-nucleic acid or ODN-to-ODN interaction, two or more hydrogen bonds with their natural partner, but only one or no hydrogen bonds with their modified SBC nucleotide partner. This is illustrated by Formulas 1a, 1b, 2a, 2b, 3a, 3b, 4a and 4b where the hydrogen bonding between natural A-T (or A-U in case of RNA) and G-C pairs, and hydrogen bonding between exemplary A'-T, T'-A, G'-C, C'-G, A'-T' and G'-C' pairs are illustrated.

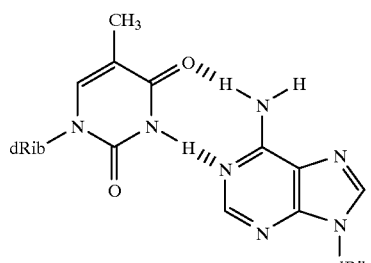

T:A

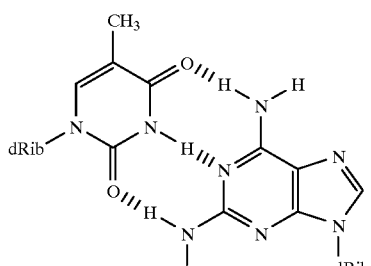

T:2-amA

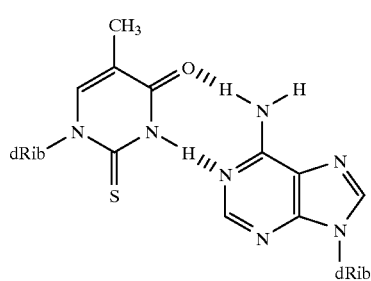

2-sT:A

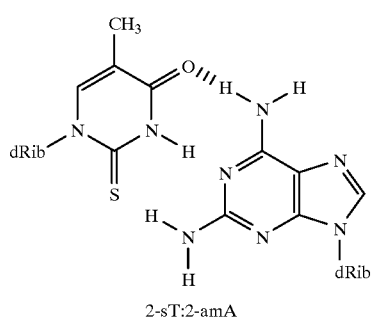

2-sT:2-amA

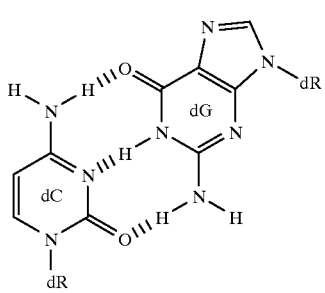

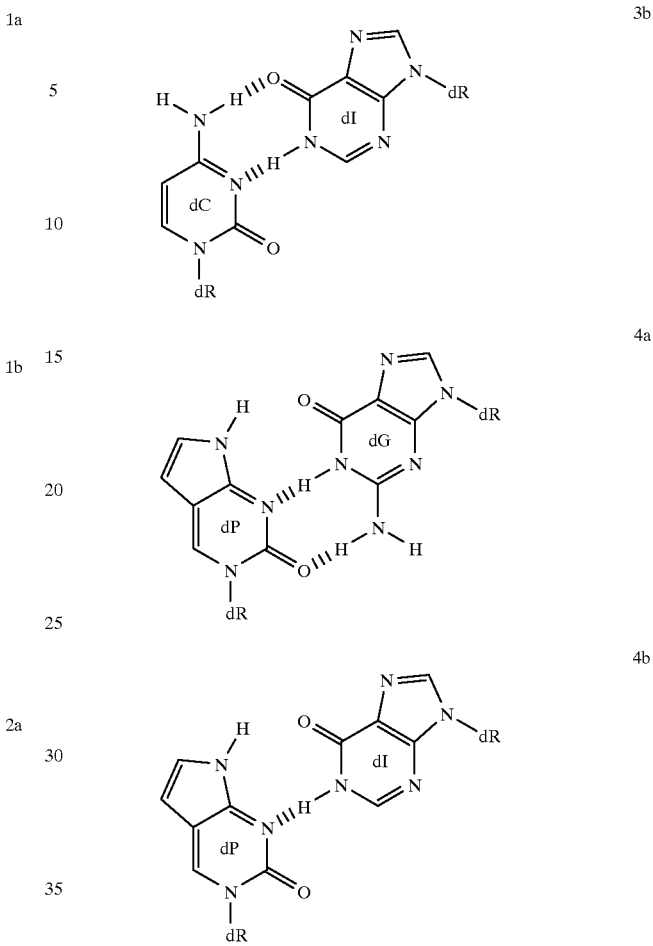

A sufficient number of the modified SBC nucleotides are incorporated such that complementary positions in both SBC ODNS are modified into a matched pair of SBC ODNs of the present invention so that the pair of the matched set does not form a stable hybrid; in other words under physiological conditions it has a melting temperature of approximately 40° C. or less. It is not necessary to replace each natural nucleotide of the ODN with a modified SBC nucleotide in order to accomplish this. Both members of the matched pair are however complementary to a target sequence in double stranded or duplex nucleic acid, where the two strands or parts of the target duplex are themselves complementary or substantially complementary to one another. As it is described in more detail below, an important use of the SBC ODNs of the present invention is hybridization with secondary structure of mRNA wherein the mRNA itself forms a duplex, such as in hairpin loops. It is known that secondary structure of mRNA and ribosomal RNA do not have two strands in the strict sense of that term. Nevertheless, unless the context otherwise indicates, in the present description the terminology "two strands" of double stranded nucleic acids also refers to the two complementary portions of duplex mRNA or of duplex ribosomal RNA as well. The general concept of double stranded DNA and of secondary structure in mRNA and ribosomal RNA is covered in this description by the term "duplex nucleic acid".

The term "RNA" can apply to any functional RNA in living organisms, such as messenger, transfer, ribosomal, small nuclear, guide, genomic, etc. RNA.

Generally speaking, the SBC ODNs of the present invention include, in addition to the modified SBC nucleotides, the naturally occurring nucleotides, and may also include some other minor naturally occurring or chemically modified nucleotides, as long as such modifications do not interfere significantly with the complementary binding ability of the ODN, as discussed above. Certain important embodiments of the SBC ODNs of the present invention include reporter groups and or cross linking functions covalently attached to one or more nucleotides of the ODN. These embodiments are described in detail below. The SBC ODNs of the present invention may include pentofuranose moieties other than ribose or 2-deoxyribose, as well as derivatives of ribose and 2-deoxyribose, for example 3-amino-2-deoxyribose, 2-fluoro-2-deoxyribose, and 2-O-$C_{1-6}$ alkyl or 2-O-allyl ribose, particularly 2-O-methyl ribose. The glycosidic linkage may be of the α or β configuration, with the β configuration being preferred. The phosphate backbone of the SBC ODNs of the present invention may include phosphorothioate linkages. Moreover, cross-linking agents, reporter groups, lipophilic groups (including cholesterol and related "steroid" derivatives) intercalators, minor groove binders as well as alkyl, hydroxy-alkyl, or amino-alkyl tails can also be attached to the 3'- or 5'- phosphate end of the SBC ODNS.

The number of nucleotide building units in the SBC ODNs of the present invention is not critical and is generally speaking, in the range of approximately 5 to 99.

A general structure for a preferred class of the modified A analog, A', within the scope of the invention and shown as a 3'-phosphate (or phosphorothioate) incorporated into the SBC ODN, is provided by Formulas 5, 6 and 7, wherein X is N or CH;

Y is O or S;

Z is OH or $CH_3$;

R is H, F, or $OR_2$, where $R_2$ is $C_{1-6}$ alkyl or allyl, or H in case of RNA, and $R_1$ is $C_{1-4}$ alkyl, $C_{1-4}$ alkoxy, $C_{1-4}$ alkylthio, F, or $NHR_3$ where $R_3$ is H, or $C_{1-4}$ alkyl, and where the 8 position of the purine, the 3 position of the pyrazolopyrimidine or the 5 position of the pyrrolopyrimidine optionally serve as point of attachment for a cross-linkig function, or reporter group as described below. A preferred embodiment of the SBC nucleotide A' has 2,6-diaminopurine (2-aminoadenine) as the base, as shown in Formula 1b. The latter nucleotide is abbreviated as 2-amA or d2-amA as applicable

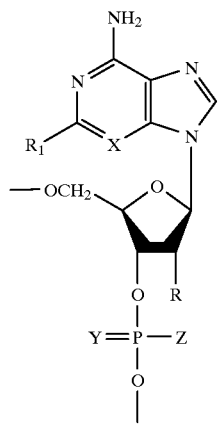

Formula 5

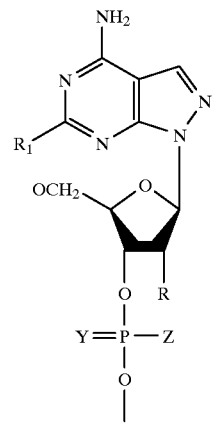

Formula 6

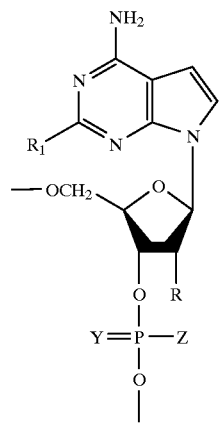

Formula 7

A general structure for a preferred class of the modified T analog, T', within the scope of the invention and shown as a 3'-phosphate (or phosphorothioate) incorporated into the BBC ODN, is provided by Formula 8, wherein Y, Z and R are defined as above, and $R_4$ is H, $C_{1-6}$ alkyl, $C_{1-6}$ alkenyl, $C_{1-6}$ alkynyl, or optionally the 5-position of the pyrimidine serves as point of attachment for a cross-linking function, or a reporter group as described below. A preferred embodiment of the SBC nucleotide T' has 2-thio-4-oxo-5-methylpyrimidine (2-thiothymine) as the base, as shown in Formula 2b. The latter nucleotide is abbreviated as 2-sT or d 2-sT as applicable.

Formula 8

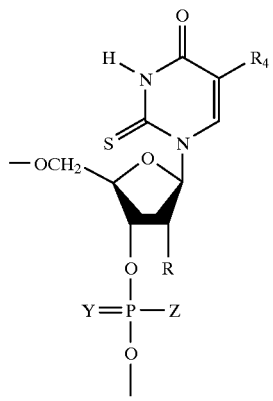

A general structure for a preferred class of the modified G analog, G', within the scope of the invention and shown as a 3'-phosphate (or phosphorothioate) incorporated into the SBC ODN, is provided by Formulas 9, 10 and 11, wherein $R_1$ is H, $C_{1-4}$ alkyl, $C_{1-4}$ alkoxy, $C_{1-4}$ alkylthio, F or $NHR_3$ where $R_3$ is defined as above, X, Y, Z and R are defined as above, and the 8 position of the purine, the 3 position of the pyrrazolopyrimidine or the 5 position of the pyrrolopyrimidine optionally serve as point of attachment for a cross-linking agent, or reporter group as described below. A preferred embodiment of the SBC nucleotide G' has 6-oxo-purine (hypoxanthine) as the base, as shown in Formula 3b. The latter nucleotide is abbreviated as I or dI as applicable.

Formula 9

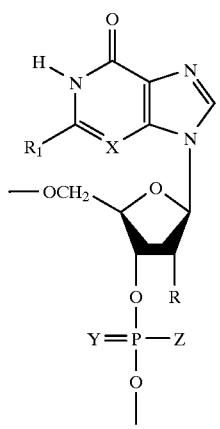

Formula 10

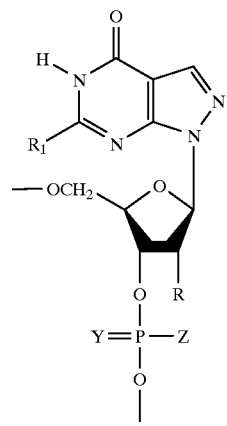

Formula 11

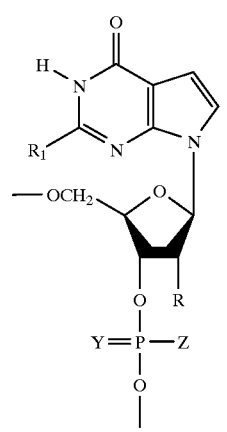

A general structure for a preferred class of the modified C analog, C', within the scope of the invention and shown as a 3'-phosphate (or phosphorothioate) incorporated into the SBC ODN, is provided by Formulas 12 and 13, wherein Y, Z, R and $R_4$ are defined as above, or optionally the 5-position of the pyrimidine serves as point of attachment for a cross-linking function, or a reporter group as described below;

$Z_1$ is O or NH, and $R_5$ is H or $C_{1-4}$ alkyl.

A preferred embodiment of the SBC nucleotide C' has pyrrolo-[2,3-d]pyrimidine-2(3H)-one as the base, as shown in Formula 4b. The latter nucleotide is abbreviated as P or dP as applicable.

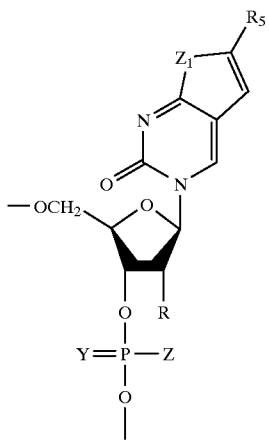

Formula 12

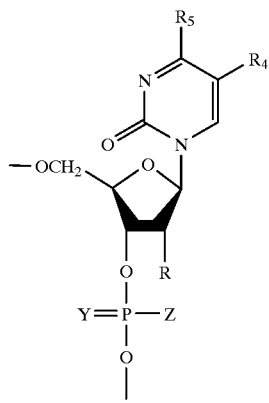

Formula 13

As noted above, the SBC ODNs of the present invention are utilized in a matched pair where the members of the pair are not covalently linked to one another. In an alternative embodiment the two members of the matched pair may be covalently linked (tethered) to one another with a covalent linkage that does not participate in hybridization and does not prevent hybridization of the two members (each of which is complementary to one target sequence of duplex nucleic acid) to the two strands of the target sequence. Linking groups which are suitable as "tethers" for linking the two BBC ODNs of a matched pair to one another include approximately selected (to avoid hydrogen bonding) nucleotide sequences having approximately 1 to 10 nucleotides. A specific example for the tether would be an ODN moiety having four T's. Alternatively the tethering linkage may comprise the grouping —[$OCH_2$—$CH_2$]$_{n"}$—0—, where n" is 1 to 10.

SBC ODNs bearing a cross-linking group

An important class of the SBC ODNs of the present invention bear a cross-linking function or group. The cross-linking function or group may be attached to a nucleotide which is itself an SBC nucleotide (as defined above) or to another type of "natural" or modified nucleotide, and the attachment may be to the heterocyclic base, to the sugar or to a phosphate, preferably a terminal phosphate moiety. The cross linking group or function serves the purpose that after hybridization of the SBC ODN to a target sequence of duplex nucleic acid, the cross-linking function covalently links the SBC ODN to the target. As it will be readily recognized by those skilled in the art, covalent cross-linking increases the efficiency and effectiveness of the SBC ODNs as probes for diagnostic, analytical or other investigative purposes, and also as therapeutic anti-sense and anti-gene agents. A cross-linking group or function may be attached to one or both members of a matched pair of SBC ODNs, and consequently one or both strands of the target sequence may become covalently bonded (alkylated) by this class of SBC ODNs.

In light of the foregoing, the cross-linking agents incorporated in the present invention meet the requirements that (1) each cross-linking agent is covalently bonded to a site on the SBC ODN, (2) its length and steric orientation is such that it reaches a suitable reaction site in the target sequence after the SBC ODN is hybridized or complexed with the target and (3) has a reactive group which reacts with a reactive nucleophilic group of the target sequence.

In the simplest terms the cross-linking agent itself may conceptually be divided into two groups or moieties, namely the reactive group, which is typically and preferably an electrophilic leaving group (L), and an "arm" ($A^*$) which attaches the leaving group L to the respective site on the SBC ODN. The leaving group L may be chosen from, for example, such groups as chloro, bromo, iodo, $So_2R'''$, or $S^+R'''R''''$, where each of $R'''$ and $R''''$ is independently $C_{1-6}$alkyl or aryl or $R'''$ and $R''''$ together form a $C_{1-6}$alkylene bridge. Chloro, bromo and iodo are preferred. Within these groups haloacetyl groups such as —$COCH_2I$, and bifunctional "nitrogen mustards", such as —N—[($CH_2$)$_2$—Cl]$_2$ are preferred. The leaving group will be altered by its leaving ability. Depending on the nature and reactivity of the particular leaving group, the group to be used is chosen in each case to give the desired specificity to the irreversibly binding probes or chemotherapeutic agents.

Although as noted above the "arm" (or linker arm) $A^*$ may conceptually be regarded as a single entity which covalently bonds the SBC ODN to the leaving group L, and maintains the leaving group L at a desired distance and steric position relative to the SBC ODN, in practice the "arm" $A^*$ may be constructed in a synthetic scheme where a bifunctional molecule is covalently linked to the SBC ODN (for example by a phosphate ester bond to the 3' or 5' terminus, or by a carbon-to-carbon bond to a heterocyclic base) through its first functionality, and is also covalently linked through its second functionality (for example an amine) to a "hydrocarbyl bridge" (alkyl bridge, alkylaryl bridge or aryl bridge, or the like) which, in turn, carries the leaving group.

A general formula of the cross linking function is thus —$A^*$—L, or —$A^*$—$L_2$ where L is the above defined leaving group and $A^*$ is a moiety that is covalently linked to the SBC ODN. The $A^*$ "arm" moiety itself should be unreactive (other than through the leaving group L) under the conditions of hybridization of the SBC ODN with the target nucleic acid sequence, and should maintain the leaving group L in a desired steric position and distance from the desired site of reaction such as an N-7 position of a guanosine residue in the target sequence. Generally speaking, the length of the $A^*$ group should be equivalent to the length of a normal alkyl chain of approximately 2 to 50 carbons.

An exemplary more specific formula for a class of preferred embodiments of the cross-linking function is —($CH_2$)$_q$—$Y^*$—($CH_2$)$_m$—L, where L is the leaving group, defined above, each of m and q is independently 0 to 8, inclusive, and where $Y^*$ is defined as a "functional linking group". A "functional linking group" is a group that has two functionalities, for example —$NH_2$ and —OH, or —COOH and —OH, or —COOH and —$NH_2$, which are capable of linking the ($CH_2$)$_q$ and ($CH2$)$_m$ bridges. An acetylenic terminus (HC≡C—) is also a suitable functionality as a precursor for $Y^*$, because it can be coupled to certain heterocycles and thereafter hydrogenated, as described below.

Other exemplary and more specific formulas for a class of preferred embodiments of the cross-linking function are —(CH$_2$)$_q$—NH—CO—(CH$_2$)$_m$—(X*)$_n$—N(R$_1$)—(CH$_2$)$_p$—L and —(CH$_2$)$_{q'}$—O—(CH$_2$)$_{q''}$—NH—CO—(CH$_2$)$_m$—(X*)$_n$—N(R$_1$)—(CH$_2$)$_p$—L where q, m and L are defined as above, q' is 3 to 7 inclusive, q" is 1 to 7 inclusive, X* is phenyl or simple substituted phenyl (such as chloro, bromo, lower alkyl or lower alkoxy substituted phenyl), n is 0 or 1, p is an integer from 1 to 6, and R$_1$ is H, lower alkyl or (CH$_2$)$_p$—L. Preferably p is 2. Those skilled in the art will recognize that the structure —N(R$_1$)—(CH$_2$)$_2$—L describes a "nitrogen mustard", which is a class of potent alkylating agents. Particularly preferred within this class of BBC ODNs of the invention are those where the cross-linking agent includes the functionality —N(R$_1$)—(CH$_2$)$_2$—L where L is halogen, preferably chlorine; and even more preferred within this class are those modified SBC ODNs where the cross linking agent includes the grouping —N—[(CH$_2$)$_2$—L]$_2$ (a "bifunctional" N-mustard).

A particularly preferred partial structure of the cross linking agent includes the grouping —CO—(CH$_2$)$_3$—C$_6$H$_4$—N—[(CH$_2$)$_2$Cl]$_2$.

In a particularly preferred embodiment the just-noted cross-linking group is attached to an n-hexylamine bearing tail at the 5' and 3' ends of the SBC ODN in accordance with the following structure:

R'—O—(CH$_2$)$_6$—NH—CO—(CH$_2$)$_3$—C$_6$H$_4$—N—[(CH$_2$)$_2$Cl]$_2$ where R' signifies the terminal 5' or 3'—phosphate group of the SBC ODN.

Other examples for the A*—L group, particularly when attached to a heterocyclic base in the oligonucleotide (such as to the 5-position of 2'-deoxyuridine) are 3-iodoacetamidopropyl, 3-(4-bromobutyramido)propyl, 4-iodoacetamidobutyl and 4-(4-bromobutyramido)butyl groups.

In accordance with other preferred embodiments, the cross-linking functionality is covalently linked to the heterocyclic base, for example to the uracil moiety of a 2'-deoxyuridylic acid building block of the SBC ODN. The linkage can occur through the intermediacy of an amino group, that is, the "arm-leaving group combination" (A*—L) may be attached to a 5-amino-2'-deoxyuridylic acid building unit of the SBC ODN. In still other preferred embodiments the "arm-leaving group combination" (A*—L) is attached to the 5-position of the 2'-deoxyuridylic acid building unit of the SBC ODN by a carbon-to-carbon bond. Generally speaking, 5-substituted-2'-deoxyuridines can be obtained by an adaptation of the general procedure of Robins et al. (*Can. J. Chem.*, 60:554 (1982); *J. Org. Chem.*, 48:1854 (1983)), as shown in Reaction Scheme 1. In accordance with this adaptation, the palladium-mediated coupling of a substituted 1-alkyne to 5-iodo-2'-deoxyuridine gives an acetylene-coupled product. The acetylenic dUrd analog is reduced, with Raney nickel for example, to give the saturated compound, which is then used for direct conversion to a reagent for use on an automated DNA synthesizer, as described below. In Reaction Scheme 1, q is defined as above, and Y' is either Y* (as defined above) or is a suitable protected derivative of Y*. Y' can also be defined as a group which terminates in a suitably protected nucleophilic function, such as a protected amine. Examples of reagents which can be coupled to 5-iodo-2'-deoxyuridine in accordance with this scheme are HC≡CCH$_2$OCH$_2$CH$_2$N(CO)$_2$C$_6$H$_4$ (phtalimidoethoxypropyne), HC≡CCH$_2$OCH$_2$CH$_2$NHCOCF$_3$ (trifluoroacetamidoethoxypropyne), HC≡CCH$_2$N(CO)$_2$C$_6$H$_4$ (phtalimidopropyne) and HC≡CCH$_2$NHCOCF$_3$ (trifluoroacetamidopropyne), In these examples the nucleosides which are obtained in this scheme are incorporated into the desired SBC ODN, and the alkylating portion of the cross-linking agent is attached to the terminal amino group of "Y'" only after removal of the respective phtalic or trifluoroacetyl blocking groups.

Another particularly preferred example of an "arm-leaving group combination" (A*—L) is attachment of a nitrogen-mustard type alkylating agent (or other alkylating agent) to the amino function of a 5-(3-aminopropyl)-2'-deoxyuridine building unit of the SBC ODN. The appropriate nucleotide building unit for ODN synthesis which includes the 5-(3-aminopropyl)-2'-deoxyuridine nucleoside moiety can be obtained in analogy to Reaction Scheme 1, and in accordance with the teaching of Meyer et al., J. Am. Chem. Soc. 1989, 111, 8517. In this particularly preferred embodiment the nucleotide having the 5-(3-aminopropyl)-2'-deoxyuridine moiety is incorporated into the SBC ODN by routine synthesis, and the cross-linking function is introduced by reacting the BBC ODN with an activated form of a "nitrogen mustard", such as 2,3,5,6-tetrafluorophenyl-4'-[bis(2-chloroethyl)amino]phenylbutyrate (Chlorambucil 2,3,5,6-tetrafluorophenyl ester; chlorambucil itself is commercially available).

Reaction Scheme 1

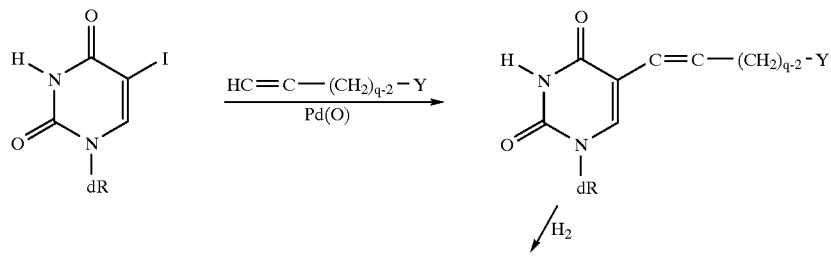

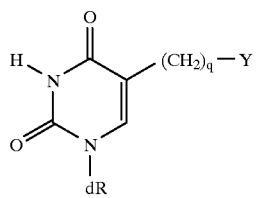

Other examples of nucleotides where the crosslinking agent is attached to a heterocyclic base, are 2'-deoxy-4-aminopyrazolo[3,4-d]pyrimidine derivatives. The general structure of these derivatives is shown below in Formula 14. A*—L represents the "arm" and the "leaving group" of the cross-linking functionality, as described above. $R_6$ represents the sugar moiety as described above, and $R_7$ and $R_8$ independently are H, OR, SR, NHOR, $NH_2$ or $NH(CH_2)_t NH_2$, where R is H or $C_{1-6}$ alkyl, t is 0 to 12. These compounds can be made from 3,4-disubstituted and 3,4,6-trisubstituted pyrazolo[3,4-d]pyrimidines, in accordance with the teaching of Kobayashi in Chem. Phar. Bull. 21:941–951 (1973) which is incorporated herein by reference.

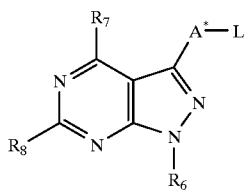

Formula 14

Discussing still in general terms the structures of the cross-linking class of SBC ODNs of the present invention, it is noted that examination of double-stranded DNA by ball-and-stick models and high resolution computer graphics indicates that the 7-position of the purines and the 5-position of the pyrimidines lie in the major groove of the B-form duplex of double-stranded nucleic acids. These positions can be substituted with side chains of considerable bulk without interfering with the hybridization properties of the bases. These side arms may be introduced either by derivatization of dThd or dCyd, or by straightforward total synthesis of the heterocyclic base, followed by glycosylation. These modified nucleosides may be converted into the appropriate activated nucleotides for incorporation into oligonucleotides with an automated DNA synthesizer. With the pyrazolo[3,4-d]pyrimidines, which are analogs of adenine, the crosslinking arm is attached at the 3-position, which is equivalent to the 7-position of purine.

The crosslinking side chain (arm=A*) should be of sufficient length to reach across the major groove from a purine 7- or 8-position, pyrimidine 5-position, pyrrolopyrimidine 5-position or pyrazolopyrimidine 3-position and react with the N-7 of a purine (preferably guanine) located above (on the oligomer 3'-side) the base pair containing the modified analog. The crosslinking side chain (arm=A*) holds the functional group away from the base when the base is paired with another within the double-stranded complex. As noted above, broadly the arm A* should be equivalent in length to a normal alkyl chain of 2 to 50 carbons. Preferably, the arms include alkylene groups of 1 to 12 carbon atoms, alkenylene groups of 2 to 12 carbon atoms and 1 or 2 olefinic bonds, alkynylene groups of 2 to 12 carbon atoms and 1 or 2 acetylenic bonds, or such groups substituted at a terminal point with nucleophilic groups such as oxy, thio, amino or chemically blocked derivatives thereof (e.g., trifluoroacetamido, phthalimido, CONR', NR'CO, and $SO_2NR'$, where R'=H or $C_{1-6}$alkyl). Such functionalities, including aliphatic or aromatic amines, exhibit nucleophilic properties and are capable of serving as a point of attachment to such groups as —$(CH_2)_m$—L,
—CO—$(CH_2)_m$—$(X^*)_n$—$N(R_1)$—$(CH_2)_p$—L, and
—CO—$CH_2$—L which are described above as components of exemplary cross-linking functional groups.

After the nucleoside or nucleotide unit which carries the crosslinking functionality A*—L, or a suitable precursor thereof, (such as the —$(CH_2)_q$—$NH_2$ or —$(CH_2)_q$—Y* group, where Y* terminates with a nucleophilic group such as $NH_2$) is prepared, further preparation of the modified oligonucleotides of the present invention can proceed in accordance with state-of-the-art. Thus, to prepare oligonucleotides, protective groups are introduced onto the nucleosides or nucleotides and the compounds are activated for use in the synthesis of oligonucleotides. The conversion to protected, activated forms follows the procedures as described for 2'-deoxynucleosides in detail in several reviews. See, Sonveaux, *Bioorganic Chemistry*, 14:274–325 (1986); Jones, in "Oligonucleotide Synthesis, a Practical Approach", M. J. Gait, Ed., IRL Press, p. 23–34 (1984).

The activated nucleotides are incorporated into oligonucleotides in a manner analogous to that for DNA and RNA nucleotides, in that the correct nucleotides will be sequentially linked to form a chain of nucleotides which is complementary to a sequence of nucleotides in target DNA or RNA. The nucleotides may be incorporated either enzymatically or via chemical synthesis. The nucleotides may be converted to their 5'-O-dimethoxytrityl-3'-(N,N-diisopropyl) phosphoramidite cyanoethyl ester derivatives, and incorporated into synthetic oligonucleotides following the procedures in "Oligonucleotide Synthesis: A Practical Approach", supra. The N-protecting groups are then removed, along with the other oligonucleotide blocking groups, by post-synthesis aminolysis, by procedures generally known in the art.

In a preferred embodiment, the activated nucleotides may be used directly on an automated DNA synthesizer according to the procedures and instructions of the particular synthesizer employed. The oligonucleotides may be prepared on the synthesizer using the standard commercial phosphoramidite or H-phosphonate chemistries. The foregoing description for preparing the SBC ODNs of the invention applies not only to the SBC ODNs which bear one or more cross linking agents, but also generally to all SBC ODNs of the invention. However, as it is described in detail below, 2-thiothymine containing SBC nucleotides (T' analogs) are more sensitive to treatment with ammonia (or other nucleophiles) than other generally used components for sequential ODN synthesis on an automatic synthesizer. The preferred methods for incorporating these components into the SBC ODNs of the invention, and other chemical processes which differ from the normally routine processes of automatic ODN synthesis, are described below.

A moiety containing the leaving group, such as a haloacyl group (CO—$CH_2$—L where L is halogen for example I) or —CO—$(CH_2)_m$—$(X^*)_n$—$N(R_1)$—$(CH_2)_p$—L group (even more preferably a CO—$(CH_2)_3$—$C_6H_4$—N—$[CH_2CH_2Cl]_2$) may be added to the aminoalkyl or like groups (—$CH_2)_q$—$Y^*$) following incorporation into oligonucleotides and removal of any blocking groups. For example, addition of an α-haloacetamide may be verified by a changed mobility of the modified compound on HPLC, corresponding to the removal of the positive charge of the amino group, and by subsequent readdition of a positive charge by reaction with 2-aminoethanethiol to give a derivative with reverse phase HPLC mobility similar to the original aminoalkyl-oligonucleotide.

In the situations where the cross linking agent ($A^*$—L moiety) is attached to the 3' or 5' terminus of the oligonucleotide, for example by an alkylamine linkage of the formula —$(CH_2)_q$—$Y^*$ ($Y^*$ terminating in an amine), the oligonucleotide synthesis may be performed to first yield the oligonucleotide with said aminoalkyl tail, to which then an alkylating moiety, such as the above-noted haloacylgroup (CO—$CH_2$—L) or —CO—$(CH_2)_m$—$(X^*)_n$—$N(R_1)$—$(CH_2)_p$—L is introduced.

SBC ODNs bearing a reporter group, lipophilic group or tail

As is known in the art a "reporter group" can be broadly defined as a group that is incorporated in, or is attached to an ODN and which renders detection or isolation of the ODN possible by application of some analytical, physical, chemical or biochemical method. Generally speaking reporter groups are attached to ODNs hen the ODNs are used as probes. In terms of attaching reporter groups to ODNs in the general sense, the art is well developed and is recited here only in a summary fashion. The SBC ODNs of the present invention having a reporter group (such as a radiactive label) attached, can be utilized substantially in accordance with state-of-the-art hybridization technology, to detect specific target sequences in duplex regions of nucleic acids. The advantage of the SBC ODNs of the present invention, as compared to the prior art, is that the SBC ODN of the present invention can effectively invade and bind to the duplex nucleic acid sequence.

Thus, probes may be labeled by any one of several methods typically used in the art. A common method of detection is the use of autoradiography with $^3H$, $^{125}I$, $^{35}S$, $^{14}C$, or 32P labeled probes or the like. Other reporter groups include ligands which bind to antibodies labeled with fluorophores, chemiluminescent agents, and enzymes. Alternatively, probes can be conjugated directly with labels such as fluorophores, chemiluminescent agents, enzymes and enzyme substrates. Alternatively, the same components may be indirectly bonded through a ligand-antiligand complex, such as antibodies reactive with a ligand conjugated with label. The choice of label depends on sensitivity required, ease of conjugation with the probe, stability requirements, and available instrumentation.

The choice of label dictates the manner in which the label is incorporated into the probe. Radioactive probes are typically made using commercially available nucleotides containing the desired radioactive isotope. The radioactive nucleotides can be incorporated into probes, for example, by using DNA synthesizers, by nick-translation, by tailing of radioactive bases in the 3' end of probes with terminal transferase or the 5'-end with a polynucleotide kinase.

Non-radioactive probes can be labeled directly with a signal (e.g., fluorophore, chemiluminescent agent or enzyme) or labeled indirectly by conjugation with a ligand. For example, a ligand molecule is covalently bound to the probe. This ligand then binds to a receptor molecule which is either inherently detectable or covalently bound to a detectable signal, such as an enzyme or photoreactive compound. Ligands and antiligands may be varied widely. Where a ligand has a natural "antiligand", namely ligands such as biotin, thyroxine, and cortisol, it can be used in conjunction with its labeled, naturally occurring antiligand. Alternatively, any haptenic or antigenic compound can be used in combination with a suitably labeled antibody. A preferred labeling method utilizes biotin-labeled analogs of oligonucleotides, as disclosed in Langer et al., *Proc. Natl. Acad. Sci. USA* 78:6633–6637 (1981), which is incorporated herein by reference.

Enzymes of interest as reporter groups will primarily be hydrolases, particularly phosphatases, esterases, ureases and glycosidases, or oxidoreductases, particularly peroxidases. Fluorescent compounds include fluorescein and its derivatives, rhodamine and its derivatives, dansyl, umbelliferone, rare earths, etc. Chemiluminescers include luciferin, acridinium esters and 2,3-dihydrophthalazinediones, e.g., luminol. A further description of reporter groups and specific examples thereof can be found in U.S. Pat. No. 5,419,966, the specification of which is expressly incorporated herein by reference.

The specific hybridization conditions are not critical and will vary in accordance with the investigator's preferences and needs. The particular hybridization technique is not essential to the invention. Hybridization techniques are generally described in "Nucleic Acid Hybridization, A Practical Approach", Hames and Higgins, Eds., IRL Press, 1985; Gall and Pardue, *Proc. Natl. Acad. Sci., U.S.A.*, 63:378–383 (1969); and John et al., *Nature*, 223:582–587 (1969). As improvements are made in hybridization techniques, they can readily be applied.

The amount of labeled probe which is present in the hybridization solution may vary widely. Generally, substantial excess of probe over the stoichiometric amount of the target duplex nucleic acid will be employed to enhance the rate of binding of the probe to the target sequence.

After hybridization at a temperature and time period appropriate for the particular hybridization solution used, the glass, plastic, or filter support to which the probe-target hybrid is attached is introduced into a wash solution typically containing similar reagents as provided in the hybridization solution. Either the hybridization or the wash medium can be stringent. After appropriate stringent washing, the correct hybridization complex may now be detected in accordance with the nature of the label.

The probe may be conjugated directly with the label. For example, where the label is radioactive, the support surface with associated hybridization complex substrate is exposed to X-ray film. Where the label is fluorescent, the sample is detected by first irradiating it with light of a particular wavelength. The sample absorbs this light and then emits light of a different wavelength which is picked up by a detector ("Physical Biochemistry", Freifelder, D., W. H. Freeman & Co., 1982, pp. 537–542). Where the label is an enzyme, the sample is detected by incubation with an appropriate substrate for the enzyme. The signal generated may be a colored precipitate, a colored or fluorescent soluble material, or photons generated by bioluminescence or chemiluminescence. The preferred label for dipstick assays generates a colored precipitate to indicate a positive reading. For example, alkaline phosphatase will dephosphorylate indoxyl phosphate which then will participate in a reduction reaction to convert tetrazolium salts to highly colored and insoluble formazans.

Detection of a hybridization complex may require the binding of a signal generating complex to a duplex of target and probe polynucleotides or nucleic acids. Typically, such binding occurs through ligand and antiligand interactions as between a ligand-conjugated probe and an antiligand conjugated with a signal.

The label may also allow indirect detection of the hybridization complex. For example, where the label is a hapten or antigen, the sample can be detected by using antibodies. In these systems, a signal is generated by attaching fluorescent or enzyme molecules to the antibodies or in some cases, by attachment to a radioactive label. (Tijssen, P., "Practice and Theory of Enzyme Immunoassays, Laboratory Techniques in Biochemistry and Molecular Biology", Burdon, R. H., van Knippenberg, P. H., Eds., Elsevier, 1985, pp. 9–20).

The amount of labeled probe present in the hybridization solution may vary widely, depending upon the nature of the label, the amount of the labeled probe that can reasonably bind to the cellular target nucleic acids, and the precise stringency of the hybridization medium and/or wash medium. Generally, substantial probe excesses over the stoichiometric amount of the target will be employed to enhance the rate of binding of the probe to the target nucleic acids.

This aspect of the invention is also directed to a method for identifying target duplex nucleic acid sequences, which method comprises utilizing an BBC ODN probe including a label as described above.

In one embodiment, the method comprises the steps of:

(a) preparing nucleic acids in the sample to be tested;

(b) hybridizing to the target nucleic acids an SBC ODN probe wherein the BBC ODN is a matched pair where each ODN of the pair is complementary to one of the two complementary strands of the target nucleic acid sequence;

(c) washing the sample to remove unbound probe;

(d) incubating the sample with detecting agents; and (e) inspecting the sample.

The above method may be conducted following procedures well known in the art.

The BBC ODNs of the present invention may also incorporate lipophilic groups, especially as a "tail" moiety attached to the 3' or 5' phosphate end of the ODN, and related tails, such as aminoalkyl groups (having approximately 3 to 20 carbons), or hydroxyalkyl groups (having approximately 3 to 20 carbons). As is known in the art, lipophilic groups are groups which due to their hydrophobic nature substantially increase lipid solubility of a compound. Examples for lipophilic groups, are long chain (3 to 20 carbon alkyl, cycloalkyl groups, and compounds having a "steroid" skeleton such as cholesterol, cholic acid, progesterone and estradiol. Further examples of lipophilic groups are menthol and retinoic acid or analogs of retinoic acid. Synthetic methods suitable for attaching lipophilic and other tail moieties to the 3' or 5' end of the SBC ODNs of the present invention are described in U.S. Pat. No. 5,419,966 the specification of which is expressly incorporated herein.

Preparation of the SBC ODNs of the Invention

The nucleosides and nucleotides shown as components of the SBC ODNs of the present invention can be made by procedures known in the chemical literature. oligonucleotide synthesis on an automatic synthesizer is generally described above in connection with the description of SBC ODNs containing a cross-linking functionality. A more detailed description of ODN synthesis with an automatic synthesizer utilizing a modified solid support, which is used in the currently preferred method for preparing the SBC ODNs of the invention, is described in U.S. Pat. No. 5,419,966.

A modification of the standard "phosphoramidite" ODN synthesis procedure is used, however, when 2—thiothymine containing SBC ODNs are prepared because this heterocycle is more base labile than the natural base heterocycles of nucleic acids. Therefore, when this nucleotide is involved, milder treatment with ammonia is required in the step of removing blocking groups from the exocyclic amino groups of the nucleotide components and to remove the SBC ODN from the solid support. The modified procedures for preparing the suitably protected "phosphoramidite" reagents of 2,6-diaminopurine-2'-deoxyribofuranoside (compounds 3 and 6) for nucleic acid synthesis are illustrated, in the alternative, in Reaction Schemes 2 and 3. As it can be seen in Reaction Scheme 2, the phenoxyacetyl blocking group is attached to the exocyclic amino groups, whereas in Reaction Scheme 3 the 9-fluorenylmethoxycarbonyl (Fmoc) protecting group is used. N-phenoxyacetyl protected 2'-deoxyguanosine and 2' deoxycytidine 3'-O-2—cyanoethyl-N,N-diisopropylphosphoramidites are available commercially from BioGenex, Alameda, Calif. 5'-O-Dimethoxytrityl-2-thiothymidine-3'-O-(2-cyanoethyl)-N,N-diisopropylphosphoramidite) can be obtained in accordance with the known literature procedure of Connolly et al. (1989) Nucleic Acids Res. 17, 4957—4974. 2,6—Diaminopurine-2'-deoxyriboside (the starting material in Reaction Schemes 2 and 3) can be obtained in accordance with the known literature procedure of Fathi et al. Tetrahedron Lett. 31, 319–322.

Reaction Scheme 2

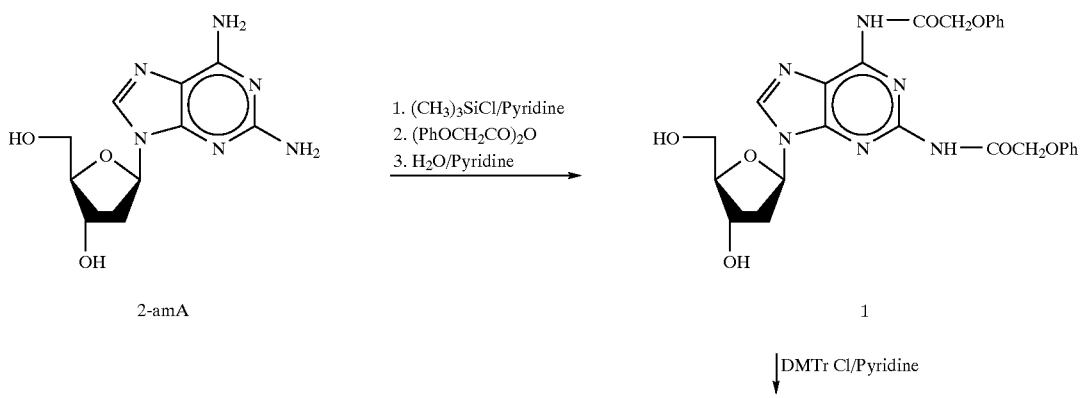

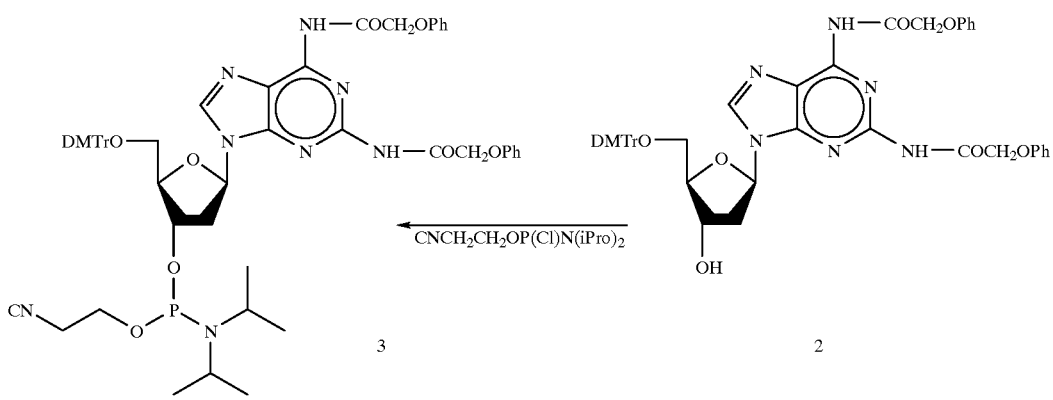

-continued

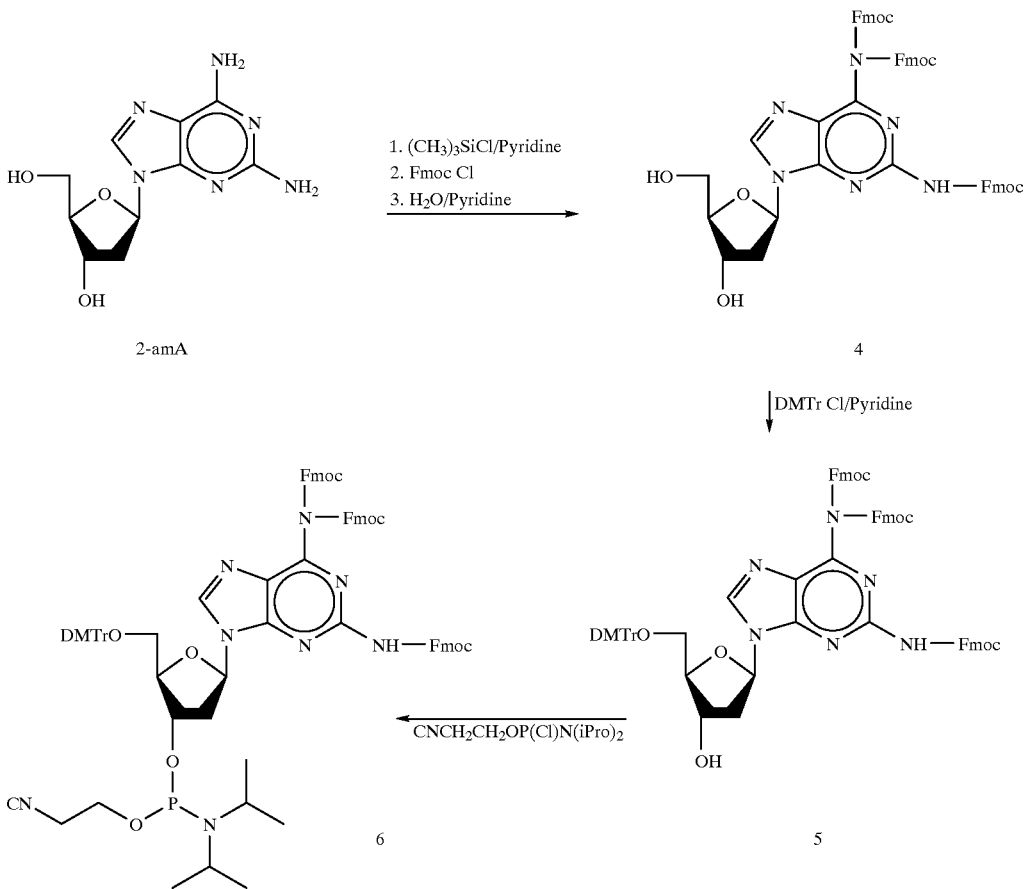

Reaction Scheme 3

The nucleotide moiety shown in Formula 4b is obtained by the method illustrated in Reaction Scheme 4 which substantially follows known chemical literature. First the "furan" analog deoxyribofuranoside, namely 3-(2'-deoxy-β-D-ribofuranosyl)furano-[2,3-d]pyrimidine-6(5H)-one (Compound 11) is synthesized by copper (I)-catalyzed cyclization from the known antiviral nucleoside 5-ethynyl-2'-deoxyuridine (Compound 10), substantially as in the literature procedure of Robins et al. J. Org. Chem. 1983, 48, 1854. This compound is dimethoxytritylated and converted into the corresponding cyanoethoxy phosphoramidite (Compound 12) suitable as a reagent for ODN synthesis, substantially by conventional literature methods (see Sinha et al. Nucleic Acids Research. 1984, 12, 4539). The SBC ODNs of the present invention are then constructed on a solid support. The final step of treating the SBC ODN with ammonia to remove protecting groups, converts the furano-[2,3-d]pyrimidine-6(5H)-one base into the pyrrolo-[2,3-d]

pyrimidine-6(5H)-one base shown in Formula 4b. The Connolly et al. Nucleic Acids Res. 1989 17, 4957–4974, Fathi et al. Tetrahedron Lett. 1990 31, 319–322, Robins et al. J. Or. Chem. 1983, 48, 1854 and Sinha et al. Nucleic Acid Research. 1984, 12, 4539 publications are expressly incorporated herein by reference.

Several oligonucleotides were prepared containing dI for dG, dP for dC, or containing d2-sT for dT and d2-amA for dA. The hybridization properties of these ODNs were studied by determining the melting temperature of the hybrids (under substantially physiological conditions) and by non-denaturing polyacrylamide gel electrophoresis (hereinafter PAGE) analysis. These measurements confirmed that each

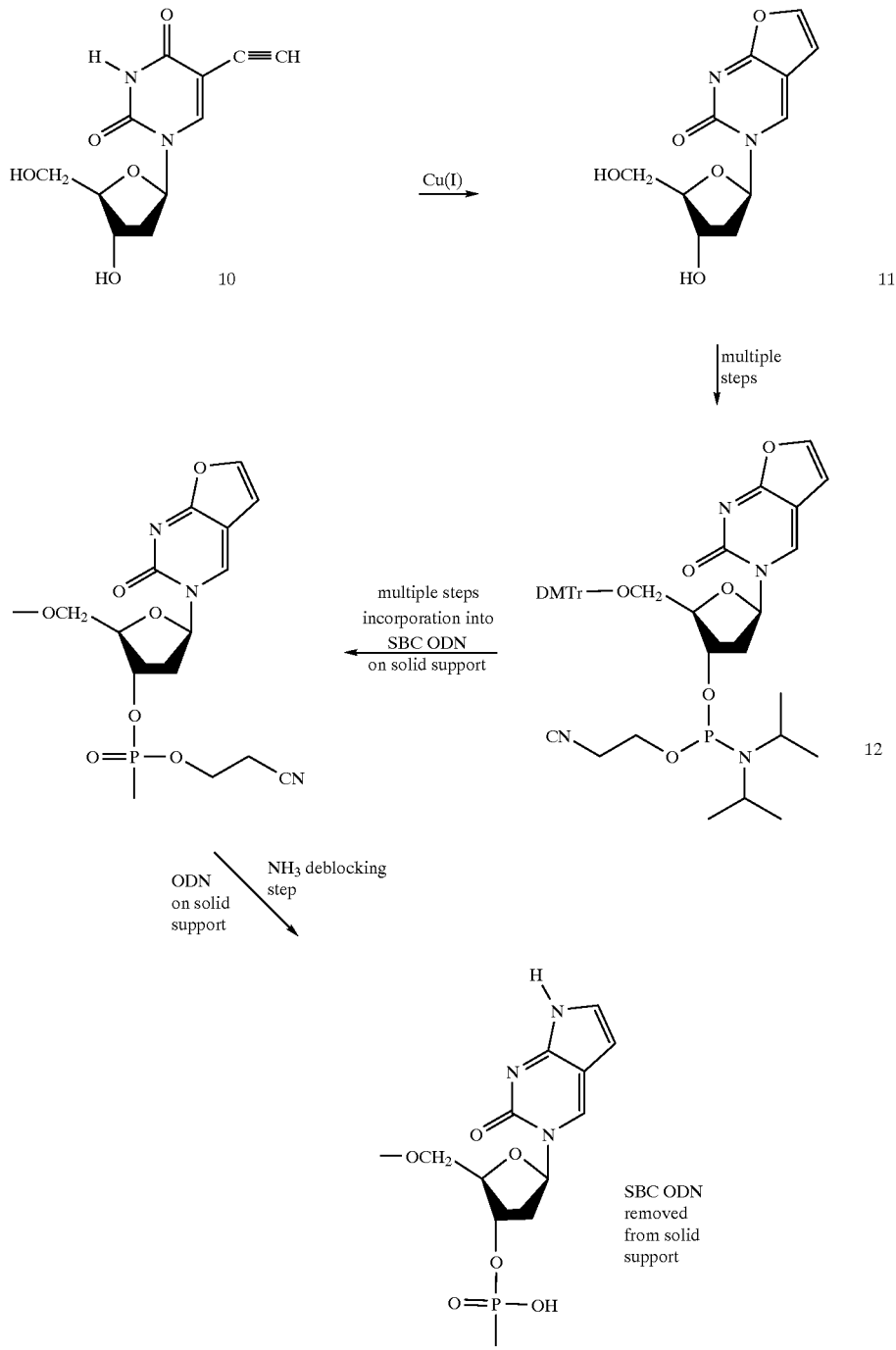

Reaction Scheme 4

Use of the SBC ODNs of the invention and evidence of sequence specific selective binding ability of the SBC ODNs forms a stable hybrid with the natural complementary or (substantially complementary) ODN, but not with the complementary SBC ODN. Thus, members of a matched pair of SBC ODNs were found to form stable hybrids with their respective natural complementary targets, but not with each other. Table 1 below indicates the melting temperatures observed under the conditions indicated in the table, and also the calculated decrease (drop) in melting temperature per modified base pair.

their unmodified complementary strands, while they do not form stable hybrids with themselves.

Table 2 refers to a complementary pair of 20-mer oligodeoxyribonucleotides (ODN V and ODN VI) which are hybridized under substantially physiological conditions (0.2M NaCl, 0.01M $Na_2HPO_4$, 0.1 mM EDTA, pH7.0, ODN concentration=$4\times10^{-7}$M). The ODNs designated in Table 2

TABLE 1

Table 1. Tm Values for Native and Modified ODNs with dI and dP

| Watson: | 5' | XTY | AXA | AXY | ATX | YYA | YYA | XXY | AAY | YAY | X | 3' |
|---|---|---|---|---|---|---|---|---|---|---|---|---|
| Crick: | 3' | YAX | TYT | TYX | TAY | XXT | XXT | YYX | TTX | XTX | Y | 5' |

| | | Watson | | Crick | | | Tm Drop per |
|---|---|---|---|---|---|---|---|
| | Hybrid | X | Y | X | Y | Tm (° C.)[a] | Modified Base Pair |
| Sequence ID NO: 1 | I | C | G | C | G | | 75.6 | 0 |
| Sequence ID NO: 3 | II | P | I | C | G | Sequence ID NO: 2 | 48.2 | 1.61 |
| Sequence ID NO: 7 | III | C | G | P | I | Sequence ID NO: 4 | 57.2 | 1.08 |
| Sequence ID NO: 8 | IV | P | I | P | I | | 20.2 | 3.26 |

[a]10 mM Tris-HCl (pH 8.0), 0.1 mM EDTA, 50 mM NaCl, 10 mM $MgCl_2$

In Table 1 the 28-mer ODN is a sequence taken from pBR 322 plasmid. Hybrid 1 is formed from complementary oligodeoxynucleotides wherein X and Y are natural dC and dG residues in both ODNs. Thus, Hybrid 1 provides a reference, to which other hybrids formed of modified SBC ODNs can be compared. The pair of SBC ODNs shown as Hybrid IV in Table 1 comprises two 28-mer sequences where each of the natural dG and dC nucleotides is replaced with dI and dP, respectively. Hybrid IV is unstable with a as SBC(V) and SBC(VI) are modified so that each dA and each dT is replaced with the d2amA and d2sT, respectively. The melting temperatures of these pairs are indicated in the Table.

TABLE 2

| Sequence ID NO: 5 | |
|---|---|
| ODN V | 5'-GTAAGAGAATTATGCAGTGC-3' |
| Sequence ID NO: 6 | |
| ODN VI | 3'-CATTCTCTTAATACGTCACG-5' |
| Sequence ID NO: 7 | |
| SBC(V) | 5'-G2sT2amA2amAG2amAG2amA2amA2sT2sT2amA2sTGC2amAG2sTGC-3' |
| Sequence ID NO: 8 | |
| SBC(VI) | 3'-C2amA2sT2sTC2sTC2sT2sT2amA2amA2sT2amACG2sTC2amACG-5' |

| | MELTING TEMPERATURE OF HYBRIDS | | | |
|---|---|---|---|---|
| | ODN(V) | ODN(VI) | SBC(V) | SBC(VI) |
| ODN(V) | — | 55° C. | — | 64° C. |
| ODN(VI) | 55° C. | — | 65° C. | — |
| SBC(V) | — | 65° C. | — | 26° C. |
| SBC(VI) | 64° C. | — | 26° C. | — | melting temperature of 20.2° C. Neverthless, each member of this pair forms a stable hybrid with its natural complement, in Hybrids II and III.

PAGE analysis also showed that the two members of the matched pair of SBC 28-mers do not hybridize in a stable manner, and that each SBC ODN and its natural complement form a stable hybrid. Moreover, the normal Watson strand showed no preference for the normal Crick strand over the SBC Crick strand because when equimolar amounts of these three strands were mixed simultaneously at room temperature about equal amounts of the duplex Hybrids I and III were formed. Additionally, there was little, if any, strand displacement or strand exchange when pre-formed Hybrid III was incubated with the normal homolog of the SBC strand, or with the Hybrid II. These data demonstrate that the SBC ODNs behave like natural ODNs when hybridized with As it can be seen, the ODNs fully modified with the preferred A' and T' modifications of the present invention exhibit even stronger binding to the natural complementary ODNs than the binding between two natural complementary strands. At the same time, the matched pair of SBC ODNs are nevertheless incapable of forming a stable hybrid with each other (their melting temperature is 26° C.

Additional experiments conducted in accordance with the present invention, in terms of melting temperature measurements and PAGE analysis, showed that a matched pair of SBC ODNs complementary to both strands of a target sequence of double stranded DNA is capable of invading the natural duplex nucleic acid to give a stable 3-armed joint. Analogous paired normal DNA ODNs failed to invade the same target. In case of long double stranded DNA, sequentially hybridizing the paired SBC ODNs to each member of the DNA target and then combining these hybrids results in stable double D loop formation which is stabilized by the bonding between each member of the SBC ODN pair and the corresponding complementary sequence in the target DNA. The resulting three-arm joints between the SBC ODNs and the DNA can be cleaved by resolvase enzymes. Strand invasion and double D-loop formation in long DNA by paired SBC ODNs is catalyzed by recombinase enzymes such as recA. Cleavage of these sites by resolvase will allow restriction of very long DNA, as from genomic DNA or cDNA libraries, at any pre-selected site. Therefore, the SBC ODNs of the invention can be used for gene mapping and like analytical and diagnostic purposes. The SBC ODNs can also be utilized to inhibit or block expression of a target gene, especially when one or preferably both members of the matched pair of SBC ODNs include a cross-linking function. In such a case, after double D loop formation with the target sequence of the gene, both strands of the nucleic acid are covalently linked to the SBC ODN, resulting in effective suppression of the gene. SBC ODNS having cross-linking functions can also be utilized for gene mapping and like diagnostic purposes.

Diagnostic and other "probe" like applications of the SBC ODNs of the invention also extend to messenger and ribosomal RNA, because a matched pair of SBC ODNs is able to sequence specifically invade the secondary structure of these duplex ribonucleic acids. Therapeutic use is in the anti-sense field, especially when the SBC ODN includes a cross-linking functionality. It is known in the art that the sequence of ribosomal RNA of bacteria is species specific. Furthermore, detection of this rRNA in DNA probe-based assays is usually hampered by lack of access of the probe to the RNA because of secondary structure. Accordingly, SBC ODNs designed to sequence specifically invade bacterial ribosomal RNA are used, in accordance with the present invention, in diagnostic applications to diagnose bacterial infections in humans and animal species.

EXPERIMENTAL SECTION—SPECIFIC EXAMPLES

Synthesis of Pyrazolo[3,4-d]pyrimidin nucleotides

Example 1
6-(Tritylamino)caproic Acid.

6-Aminocaproic acid (26 g, 0.2 mole) was dissolved in dichloromethane (200 mL) by the addition of triethylamine (100 mL). Trityl chloride (120 g, 0.45 mole) was added and the solution stirred for 36 hours. The resulting solution was extracted with 1N HCl and the organic layer evaporated to dryness. The residue was suspended in 2-propanol/1N NaOH (300 mL/100 mL) and refluxed for 3 hours. The solution was evaporated to a thick syrup and added to dichloromethane (500 mL). Water was added and acidified. The phases were separated, and the organic layer dried over sodium sulfate and evaporated to dryness. The residue was suspended in hot 2-propanol, cooled, and filtered to give 43.5 (58%) of 6-(tritylamino)caproic acid, useful as an intermediate compound.

Example 2
5-(Tritylamino)pentylhydroxymethylenemalononitrile.

To a dichloromethane solution of 6-(tritylamino)-caproic acid (20.0 g, 53 mmole) and triethylamine (20 mL) in an ice bath was added dropwise over 30 min isobutylchloroformate (8.3 mL, 64 mmole). After the mixture was stirred for 2 hours in an ice bath, freshly distilled malononitrile (4.2 g, 64 mmole) was added all at once. The solution was stirred for 2 hours in an ice bath and for 2 hours at RT. The dichloromethane solution was washed with ice cold 2N HCl (300 mL) and the biphasic mixture was filtered to remove product that precipitated (13.2 g). The phases were separated and the organic layer dried and evaporated to a thick syrup. The syrup was covered with dichloromethane and on standing deposited fine crystals of product. The crystals were filtered and dried to give 6.3 g for a total yield of 19.5 g (87%) of the product, which is useful as an intermediate.

Example 3
5-(Tritylamino)pentylmethoxymethylenemalononitrile.

A suspension of the malononitrile of Example 2 (13 g, 31 mmole) in ether/dichloromethane (900 mL/100 mL), cooled in an ice bath, was treated with a freshly prepared ethereal solution of diazomethane (from 50 mmole of Diazald$^R$ (Aldrich Chemical Company)). The solution was stirred for 6 hours and then neutralized with acetic acid (10 mL). The solution was evaporated to dryness and the residue chromatographed on silica gel using dichloromethane/acetone (4/1) as the eluent. Fractions containing product were pooled and evaporated to a syrup. The syrup was triturated with dichloromethane to induce crystallization. The crystals were filtered an dried to give 8.3 g (61%) of chromatographically pure product, useful as an intermediate compound.

Example 4
5-Amino-3-[(5-tritylamino)pentyl]pyrazole-4-carbonitrile.

To a methanol solution (100 mL) of the product of Example 3 (7.0 g, 16 mmole) in an ice bath was added hydrazine monohydrate (7.8 mL, 160 mmole) dropwise over 15 min. After stirring for 30 min in an ice bath, the solution was evaporated to dryness. The residue was suspended in cold methanol and filtered to give 7.1 g (100%) of 5-amino-3-[(5-tritylamino)pentyl]pyrazole-4-carbonitrile, useful as an intermediate, after drying. An analytical sample was prepared by recrystallization from water.

Example 5
5-Amino-1-(2-deoxy-3,5-di-O-toluoyl-β-D-erythropentofuranosyl)-3-[(5-tritylamino) pentyl]pyrazole-4-carbonitrile.

An ice cold solution of the carbonitrile from Example 4 (3.5 g, 8 mmole) was treated with sodium hydride and stirred for 30 min at 0–4° C. 1-Chloro-1,2-dideoxy-3,5-di-O-toluoylribofuranose was added and the solution stirred for 1 hour at 0–4° C. The solution was poured into a saturated solution of sodium bicarbonate and extracted with dichloromethane. The organic layer was dried over sodium sulfate and evaporated to dryness. The residue was flash chromatographed. The organic layer was dried over sodium sulfate and evaporated to dryness. The residue was flash chromatographed on silica gel using toluene/ethyl acetate (5/1) as eluent. Two major products were isolated and identified as the N-1 and N-2 isomers in 57% (3.6 g) and 20% (1.2 g) N-1 and N-2 yields, respectively. Approximately 1 g of a mixture of N-1 and N-2 isomers was also collected. Overall yield of glycosylated material was 5.8 g (92%). The N-1 isomer, 5-amino-i-(2-deoxy-3,5-di-o-toluoyl-β-D-erythropentofuranosyl)-3-[(5-tritylamino)-pentyl]pyrazole-4-carbonitrile, was used without further purification in Example 6.

Example 6
1-(2-Deoxy-β-D-erythropentofuranosyl)-3-[5-(tritylamino)-pentyl]pyrazolo[3,4-d]pyrimidin-4-amine.

To a toluene (100 mL) solution of the pyrazole-4-carbonitrile of Example 5 (3.5 g, 4.4 mmole) was added diethoxymethyl acetate (1.1 mL, 6.7 mmole). The solution was kept at 80–90° C. for 5 hours and then evaporated to a syrup. The syrup was dissolved in dichloromthane (10 mL) and added to ice cold methanolic ammonia (100 mL) in a glass pressure bottle. After two days at RT the contents of the bottle were evaporated to dryness. The residue was dissolved in methanol and adjusted to pH 8 with freshly prepared sodium methoxide to complete the deprotection. After stirring overnight the solution was treated with Dowex$^R$-50 H+ resin, filtered and evaporated to dryness. The residue was chromatographed on silica gel using acetone/hexane (3/2) as eluent to give 2.0 g (77%) of analytically pure product.

Example 7
1-(2-Deoxy-β-D-erythropentofuranosyl)-3-[5-(tritylamino)-pentyl]pyrazolo[3,4-d]pyrimidin-4-amine 5'-monophosphate.

To an ice cold solution of the pyrazolopyrimidin-4-amine of Example 6 (250 mg, 0.43 mmole) in trimethyl phosphate (5 mL) was added phosphoryl chloride (50 μL) and the solution was kept at 0–4° C. The reaction was monitored by reversed phase HPLC using a linear gradient from 0 to 100% acetonitrile in water over 25 min. After stirring for 5 hours, an additional aliquot of phosphoryl chloride (25 μL) was added and the solution was stirred another 30 min. The solution was poured into 0.1M ammonium bicarbonate and kept in the cold overnight. The solution was then extracted with ether and the aqueous layer evaporated to dryness. The residue was dissolved in water (5 mL) and purified by reversed phase HPLC using a 22 mm×50 cm C18 column. The column was equilibrated in water and eluted with a gradient of 0 to 100% acetonitrile over 20 min. Fractions containing the desired material were pooled and lyophilized to give 160 mg (56%) of chromatographically pure nucleotide.

Example 8
1-(2-Deoxy-β-D-erythropentofuranosyl)-3-{5-[(6-biotinamido)hexanamido]pentyl}pyrazolo[3,4-d]pyrimidin-4-amine 5'-monophosphate.

An ethanol solution (10 mL) of the nucleotide of Example 7, palladium hydroxide on carbon (50 mg), and cyclohexadiene (1 mL) was refluxed for 3 days, filtered, and evaporated to dryness. The residue was washed with dichloromethane, dissolved in DMF (1.5 mL) containing triethylamine (100 mL), and treated with N-hydroxysuccinimidyl biotinylaminocaproate (50 mg). After stirring overnight an additional amount of N-hydroxysuccinimidyl 6-biotinamidocaproate (50 mg) was added and the solution was stirred for 18 hours. The reaction mixture was evaporated to dryness and chromatographed following the procedure in Example 7. Fractions were pooled and lyophilized to give 80 mg of chromatographically pure biotinamido-substituted nucleotide.

Example 9
1-(2-Deoxy-β-D-erythropentofuranosyl)-3-[5-(6-biotinamido)-hexanamidopentyl]pyrazolo[3,4-d]pyrimidin-4-amine 5'-triphosphate.

The monophosphate of Example 8 (80 mg, ca. 0.1 mmole) was dissolved in DMF with the addition of triethylamine (14 μL). Carbonyldiimidazole (81 mg, 0.5 mmole) was added and the solution stirred at RT for 18 hours. The solution was treated with methanol (40 μL), and after stirring for 30 minutes tributylammonium pyrophosphate (0.5 g in 0.5 mL DMF) was added. After stirring for 24 hours another aliquot of tributylammonium pyrophosphate was added and the solution was stirred overnight. The reaction mixture was evaporated to dryness and chromatographed following the procedure in Example 8. Two products were collected and were each separately treated with conc. ammonium hydroxide (1 mL) for 18 hours at 55° C. UV and HPLC analysis indicated that both products were identical after ammonia treatment and were pooled and lyophilized to give 35.2 mg of nucleoside triphosphate.

Example 10
Nick-Translation Reaction

The triphosphate of Example 9 was incorporated into pHPV-16 using the nick translation protocol of Langer et al. (supra). The probe prepared with the triphosphate of Example 9 was compared with probe prepared using commercially available bio-11-dUTP (Sigma Chemical Co). No significant differences could be observed in both a filter hybridization and in in situ smears.

More specifically, the procedure involved the following materials and steps

Materials:
DNase (ICN Biomedicals)—4 μg/mL
DNA polymerase 1 (U.S. Biochemicals)—8 U/mL
pHPV-16—2.16 mg/mL which is a plasmid containing the genomic sequence of human papillomavirus type 16.
10×-DP—1M Tris,pH 7.5(20 mL); 0.5M OTT(80 mL); 1M MgCl$_2$(2.8 mL); H$_2$O (17mL)
Nucleotides—Mix A—2 mM each dGTP, dCTP, TTP (Pharmacia) Mix U—2 mM each dGTP, DcTP, dATP
Bio-11-dUTP—1.0 mg/mL (BRL)
Bio-12-dAPPTP—1.0 mg/mL Steps:
To an ice cold mixture of 10×-DP (4 mL), pHV-16 (2 mL), nucleotide mix A (6 mL), Bio-12-dAPPTP (2 mL), and H$_2$O (20 mL) was added DNase (1 mL) and DNA polymerase 1 (2.4 mL). The reaction mixture was incubated at 16° C. for 1 hour. The procedure was repeated using Bio-11-dUTP and nucleotide mix U in place of Bio-12-dAPPTP (comprising the triphosphate of Example 9) and nucleotide mix A.

Nucleic acid was isolated by ethanol precipitation and hybridized to pHPV-16 slotted onto nitrocellulose. The hybridized biotinylated probe was visualized by a streptavidin-alkaline phosphatase conjugate with BCIP/NBT substrate. Probe prepared using either biotinylated nucleotide gave identical signals. The probes were also tested in an in situ format on cervial smears and showed no qualitative differences in signal and background.

Example 11
5-Amino-3-[(5-tritylamino)pentyl]pyrazole-4-carboxamide.

Following the procedure of Example 2, except that cyanoacetamide is used instead of malononitrile, 5-(tritylamino)pentylhydroxymethylececyanoacetamide is prepared from 6-(tritylamino)caproic acid. This is then treated with diazomethane to give the methoxy derivative, following the procedures of Example 3, which is then reacted with hydrazine monohydrate, as in Example 4, to give 5-amino-3-[(5-tritylamino)-pentyl]pyrazole-4-carboxamide.

Example 12
4-Hydroxy-6-methylthio-3-[(5-tritylamino)pentyl]pyrazolo-[3,4-d]pyrimidine.

The carboxamide from Example 11 is reacted with potassium ethyl xanthate and ethanol at an elevated temperature to give the potassium salt of 4-hydroxypyrazolo[3,4-d]pyrimidine-6-thiol. This salt is then reacted with iodomethane to give 4-hydroxy-6-methylthio-3-[(5-tritylamino)pentyl]pyrazolo[3,4-d]pyrimidine.

Example 13

1-(2-Deoxy-β-D-erythropentofuranosyl)-4-hydroxy-3-[5-(tritylamino)pentyl]pyrazolo[3,4-d]pyrimidin-6-amine.

Following the procedure of Example 5, the pyrazolopyrimidine of Example 12 is treated with sodium hydride and reacted with 1-chloro-1,2-dideoxy-3,5-di-O-toluoylribofuranose. The resulting compound is reacted with MCPBA and with methanolic ammonia, and the toluoyl protecting groups are removed to give the product.

Example 14

1-(2-Deoxy-β-D-erythropentofuranosyl)-4-hydroxy-3-[5-(6-biotinamido)hexanamidopentyl]pyrazolo[3,4-d]pyrimidin- 6-amine 5'-monophosphate.

Following the procedure of Example 7, the pyrazolopyrimidine of Example 13 is reacted with phosphoryl chloride to give the corresponding 5'-monophosphate.

Following the procedure of Example 8, the above 5'-monophosphate is reacted with palladium/carbon and cyclohexadiene, and the residue is reacted with N-hydroxysuccinimidyl biotinylaminocaproate to give 1-(2-deoxy-β-D-erythropentofuranosyl)-4-hydroxy-3-[5-(6-biotinamido) hexanamidopentyl]pyrazolo[3,4-d]pyrimidin-6-amine 5'-monophosphate.

Example 15

1-(2-Deoxy-β-D-erythropentofuranosyl)-4-hydroxy-3-[5-(6-biotinamido hexanamidopentyl]pyrazolo[3,4-d] pyrimidin-6-amine 5'-triphosphate.

Following the procedure of Example 9, the 5'-monophosphate of Example 14 is treated with carbonyldiimidazole and then reacted with tributylammonium pyrophosphate to give the corresponding 5'-triphosphate.

Example 16

1-(2-Deoxy-β-D-erythropentofuranosyl)-3-[5-(tritylamino)-pentyl]pyrazolo[3,4-d]pyrimidine-4-benzylamine.

1-(2-Deoxy-β-D-erythropentofuranosyl)-3-[5-(tritylamino)pentyl]pyrazolo[3,4-d]pyrimidine-4-amine from Example 6 is reacted with benzoyl chloride and pyridine to give 1-(2-deoxy-3,5-di-o-benzoyl-β-D-erythropentofuranosyl)-3-[5-(tritylamino)pentyl]pyrazolo-[3,4-d]-pyrimidine-4-dibenzoylamine. This is treated with aqueous sodium hydroxide to partially deprotect the compound giving 1-(2-deoxy-β-D-erythropentofuranosyl)-3-[5-(tritylamino)pentyl]pyrazolo[3,4-d]pyrimidine-4-benzoylamine.

Example 17

1-(2-Deoxy-β-D-erythropentofuranosyl)-3-[5-(trifluoroacetamido)pentyl]pyrazolo[3,4-d]pyrimidine-4-benzoylamine.

Following the procedure of Example 8, the benzoylamine of Example 16 is treated with palladium hydroxide on carbon and then with trifluoroacetic anhydride to give 1-(2-deoxy-β-D-erythropentofuranosyl)-3-[5-(trifluoroacetamido)pentyl]pyrazolo[3,4-d]pyrimidine-4-benzoylamine.

Example 18

1-(2-Deoxy-5-O-dimethoxytrityl-β-D-erythropentofuranosyl)-3-[5-(trifluoroacetamido)pentyl]pyrazolo[34-d]pyrimidine-4-benzylamine 3'-O-(N,N-diisopropyl)phosphoramidite cyanoethyl ester.

The compound of Example 17 is reacted with dimethoxytrityl chloride and pyridine to give the corresponding 5'-dimethoxytrityl compound. This compound is then reacted with cyanoethyl chloro-N,N-diisopropylphosphoramidite (according to the method of Sinha et al., *Nucleic Acids Res.*, 12:4539 (1984)) to give the 3'-O-activated nucleoside.

Synthesis of nucleotides and ODNs including a cross-linking function

Example 19

5-(4-Phthalimidobut-1-yn-1-yl)-2'-deoxyuridine

5-Iodo-2'-deoxyuridine (354 mg, 1 mmol) was dissolved in 10 mL of dimethylformamide. Cuprous iodide (76 mg, 0.4 mmol), tetrakis (triphenylphosphine) palladium (0) (230 mg, 0.2 mmol), and triethylamine (200 mg, 2.0 mmol) were added. 4-Phthalimidobut-1-yn (300 mg, 1.5 mmol) was added all at once and the reaction kept at 60° C. for three hours. The clear yellow reaction was then evaporated and methylene chloride was added. Scratching of the flask induced crystallization of nearly all of the product which was filtered and recrystallized from 95% ethanol to give 335 mg (78%) of title compound as fine, feathery needles.

Example 20

5-(4-Phthalimidobut-1-yl)-2'-deoxyuridine 1.00 Gram of 5-(4-Phthalimidobut-1-yn-1-yl)-21-deoxyuridine was dissolved in 95% EtOH and about 3 g of neutral Raney nickel was added. After 48 hours, the catalyst was removed by cautious filtration and the filtrate was evaporated to a solid which was recrystallized from methanol-water to give 960 mg (97%) of the title compound.

Example 21

5-(3-Iodoacetamidopropyl)-2'-deoxyuridine.

5-(3-Trifluoroacetamidoprop-1-yl)-2'-deoxyuridine (0.3 mmol) is treated with ammonia and then with N-hydroxysuccinimidyl α-iodoacetate (0.5 mmol). The reaction mixture is evaporated to dryness and purified by chromatography to give 5-(3-iodoacetamidopropyl)-2'-deoxyuridine.

Example 22

5-(4-(4-Bromobutyramido)butyl)-2'-deoxyuridine 5-(4-phthalimidobut-1-yl)-2'-deoxyuridine is treated with ammonia and then with N-hydroxysuccinimidyl-4-bromobutyrate to give 5-(4-(4-bromobutyramido)butyl)-2'-deoxyuridine.

Preparation of Synthetic Oligonucleotides

Example 23

Phosphoramidite Preparation and DNA Synthesis.

Nucleosides were 5'-dimethoxytritylated, following known procedures, to give around 85% yield, and the 3'-phosphoramidite was made using diisopropylamino β-cyanoethylchlorophosphite (as described in "Oligonucleotide Synthesis: A Practical Approach", supra) with diisopropylethylamine in methylene chloride. The phosphoramidite was made into a 0.2N solution in acetonitrile and placed on the automated DNA synthesizer. Incorporation of these new and modified phosphoramidites gave incorporation similar to ordinary phosphoramidites (97–99% as judged by assay of the trityl color released by UV.)

Oligonucleotides were removed from the DNA synthesizer in tritylated form and deblocked using 30% ammonia at 55° C. for 6 hours. Ten μL of 0.5M sodium bicarbonate was added to prevent acidification during concentration. The oligonucleotide was evaporated to dryness under vacuum and redissolved in 1.0 mL water. The oligonucleotides were purified by HPLC using 15–55% acetonitrile in 0.1N triethylammonium acetate over 20 minutes. Unsubstituted oligonucleotides came off at 10 minutes; amino derivatives took 11–12 minutes. The desired oligonucleotide was collected and evaporated to dryness, then it was redissolved in 80% aqueous acetic acid for 90 minutes to remove the trityl group. Desalting was accomplished with a G25 Sephadex column and appropriate fractions were taken. The fractions were concentrated, brought to a specific volume, dilution reading taken to ascertain overall yield and an analytical HPLC done to assure purity. oligonucleotides were frozen at −20° C. until use.

In general, to add the crosslinking arm to an aminoalkyloligonucleotide, a solution of 10 μg of the aminoalkyloligonucleotide and a 100X molar excess of n-hydroxysuccinimide haloacylate such as α-haloacetate or 4-halobutyrate in 10 μL of 0.1M borate buffer, pH 8.5, is incubated at ambient temperature for 30 min. in the dark. The entire reaction is passed over a NAP-10 column equilibrated with and eluted with distilled water. Appropriate fractions based on UV absorbance are combined and the concentration is determined spectrophotometrically.

2,3 5,6-Tetrafluorophenyl trifluoroacetate.

A mixture of 2,3,5,6-tetrafluorophenol (55.2 g, 0.33 mol), trifluoroacetic anhydride (60 mL, 0.42 mol) and boron trifluoride etherate (0.5 mL) was refluxed for 16 hr. Trifluoroacetic anhydride and trifluoroacetic acid were removed by distillation at atmospheric pressure. The trifluoroacetic anhydride fraction (bp 40° C.) was returned to the reaction mixture along with 0.5 mL of boron trifluoride etherate, and the mixture was refluxed for 24 hr. This process was repeated two times to ensure complete reaction. After distillation at atmospheric pressure, the desired product was collected at 62° C./45 mm (45° C./18 mm) as a colorless liquid: yield=81.3 g (93%); d=1.52 g/mL; $n_D^{21}$=1.3747; IR (CHCl$_3$) 3010, 1815, 1525, 1485, 1235, 1180, 1110, and 955 cm$^{-1}$. Anal. Calcd for $C_8HF_7O_2$: C, 36.66; H, 0.38; F, 50.74. Found: C, 36.31; H, 0.43; F, 50.95.

2,3,5 6-Tetrafluorophenyl-4'-[bis(2-chloroethyl)amino] phenylbutyrate (Chlorambucil 2,3,5,6-tetrafluorophenyl ester)

To a solution of 0.25 g (0.82 mmol) of chlorambucil (supplied by Fluka A. G.) and 0.3 g (1.1 mmol) of 2,3,5,6-tetrafluorophenyl trifluoroacetate in 5 ml of dry dichloromethane was added 0.2 Ml of dry triethylamine. The mixture was stirred under argon at room temperature for 0.5 h and evaporated. The residual oil was purified by column chromatography on silica gel with hexane-chloroform (2:1) as the eluting solvent to give the ester as an oil: 0.28 g (75%); TLC on silica gel (CHCl$_3$) R$_f$0.6; IR (in CHCl$_3$) 3010, 1780, 1613, 1521, 1485 cm$^{-1}$.

2-Propargyloxyethyl)amine (John, R., and Seitz, G., Chem. Ber., 123, 133 (1990) was prepared by condensing propynol with 2-bromoethylammonlum bromide in liquid ammonia in the presence of Na NH$_2$, and was used crude for the next reaction.

3-(2-Trifluoroacetamidoethoxy)propyne (2-Propargyloxyethyl)amine (13.8 g, 0.14 mol) is stirred and chilled in an iso-propanol-dry ice bath while excess of trifluoroacetic anhydride (26 ml, 0.18 mol) is added dropwise. N-(2-Propargyloxyethyl)trifluoroacetamide is distilled at 84–85°/1.7 torr as an oil which solidified upon refrigeration; yield 14.4 g (52%), m.p. (160, $n_D^{24}$ 1.4110. Anal. Calcd. for $C_7H_8F_3NO_2$: C, 43.09, H, 4.13; N, 7.18; F, 29.21. Found: C, 42.80; H, 4.03; N, 7.06; F, 29.38.

5-[3-(2-Trifluoroacetamidoethoxy),Propynyl]-2'-deoxyuridine

A mixture of 5-iodo-2'-deoxyuridine (3.54 g, 10 mmol), copper(l) iodide (0.19 g, 1 mmol) and tetrakis (triphenylphosphine)palladium(O) (0.58 g, 0.5 mmol) is dried in vacuo at 60° for 3 hours and placed under argon. A suspension of the mixture in dry DMF (20 ml) is stirred under argon and treated with dry triethylamine (1.7 ml, 12 mmol) followed by 3-(2-Trifluoroacetamidoethoxy)propyne (3.17 g, 16 mmol). The mixture is cooled at room temperature in a water bath and stirred for 17 hours. The mixture is treated with 2% acetic acid (100 ml), the catalyst is removed by filtration and washed with 50% methanol. The filtrates are combined and passed onto a LiChroprep RP-18 column (5×25 cm), the column is washed, then eluted with 1% acetic acid in 50% (v/v) methanol. The fractions with the main product are combined, evaporated, and dried in vacuo. The resultant foam is stirred with 150 ml of ether to give crystalline product; yield 3.6 g (85%); m.p. 145–1520.

5-[3-(2-Trifluoroacetamidoethoxy)propyl]2'-deoxyuridine

A solution of 5-[3-(2-trifluoroacetamidoethoxy) propynyl]-2'-deoxyuridine (3.4 g, 8.1 mmol) in methanol (20 ml) is stirred with ammonium formate (prepared by addition of 3 ml, 79 mmol of cold 98% formic acid into 2 ml, 50 mmol of dry ice frozen 25% ammonia) and 0.2 g of 10% Pd/C for 7 hours at room temperature under hydrogen atmosphere. The catalyst is removed by filtration, the filtrate evaporated and product is purified on LiChroprep RP-18 column by the above procedure. Fractions containing the desired product are combined and evaporated to dryness in vacuo and the resultant solid is triturated with dry ether to give 3.0 g (87% product, m.p. 107–110°; max in nm, in 0.1M triethylamine-acetate (pH 7.5), 220, 268. Analysis calculated for $C_{16}H_{22}F_3N_3O_7$: C, 45.18; H, 5.21; N, 9.88; F, 13.40. Found C, 45.16; H, 5.16; N, 9.68; F, 13.13.

Introduction of chlorambucil residue into the primary amino groups of oligonucleotides Preparation of the cetyltrimethylammonium salt of oligonucleotides: a 100 μL aliquot of aqueous solution of oligonucleotide (50–500 ug), generally triethylammonium salt, was injected to a column packed with Dowex 50wx8 in the cetyltrimethylammonium form and prewashed with 50% alcohol in water. The column was eluted by 50% aqueous ethanol (0.1 mL/min). Oligonucleotide containing fraction was dried on a Speedvac over 2 hours and used in following reactions.

Ethanol solution (50 uL) of cetyltrimethylammonium salt of an oligonucleotide (50–100 μg) was mixed with 0.08M solution of 2,3,5,6-tetrafluorophenyl-4'-[bis(2-chloroethyl) amino]phenylbutyrate (tetrafluorophenyl ester of chlorambucil) in acetonitrile (50 μL) and 3 μL of diisopropylethylamine. After shaking for three hours at room temperature, the product was precipitated by 2% LiClO$_4$ in acetone (1.5 mL). The product was reprecipitated from water (60 uL) by 2% LiClO$_4$ in acetone three times. Finally the chlorambucil derivative of the oligonucleotide was purified by Reverse Phase Chromatography with approximately 50–80% yield. The fraction containing the product was concentrated by addition of butanol. The isolated chlorambucil derivative of the oligonucleotide was precipitated in acetone solution with LiClO$_4$, washed by acetone and dried under vacuum. All manipulations of reactive oligonucleotide were performed as quickly as possible, with the product in ice-cold solution.

Preparation of SBC ODNs

N-phenoxyacetyl protected 2'-deoxyguanosine and 2'-deoxycytidine 3'-O-2-cyanoethyl-N,N'-diisopropylphosphoramidite are available commercially from BioGenex, Alameda, California. 5'-O-dimethoxytrityl-2-thiothymidine-3'-O-(2-cyanoethyl-N,N'-diisopropylphosphoramidite) was prepared using the procedure of Connolly et al. supra. 2,6-diaminopurine-2'-deoxyriboside was synthesized as described by Fathi et al. supra.

$N^2,N^6$-bis(phenoxyacetyl)-2,6-diaminopurine-2'-deoxyriboside (Compound 1, Reaction Scheme 1).

This compound is prepared substantially in accordance with the literature procedure of Schulhof et al.(1987) Nucleic Acids Res. 15, 397–416. 2,6-Diaminopurine-2'-deoxyriboside (1.8 g, 6.8 mmol) is dried by evaporation with dry pyridine. Trimethylchlorosilane (5 mL, 39 mmol) is added dropwise to an ice cold solution of 2,6-diaminopurine-2'-deoxyriboside in 35 mL of dry pyridine. After 30 min, phenoxyacetic anhydride (8.0 g, 28 mmol) is added to the stirred solution. The mixture is kept for 3 h at RT then cooled to 5° C. Water (5 mL) is added to quench the excess of phenoxyacetic anhydride. After being stirred for 2 h, the reaction mixture is concentrated on a rotary evaporator to approximately 10 mL and then diluted with water to 120 mL to give an emulsion. The emulsion is washed with ether (150 mL). The resulting precipitate is filtered, washed with ether, water, and dried in vacuo. The material (3.2 g, 87%) obtained by using this procedure is pure enough to be used in the next step without additional purification.

5'-O-Dimethoxytrityl-$N^2,N^6$-bis(phenoxyacetyl)-2,6-diaminopurine-2'-deoxyriboside (Compound 2).

$N^2,N^6$-bis(phenoxyacetyl)-2,6-diaminopurine-2'-deoxyriboside (3.2 g, 5.8 mmol) is dried by evaporation with dry pyridine (2×20 mL) and dissolved in 30 mL of the same solvent. 4,4'-dimethoxytrityl chloride (2.0 g, 6 mmol) is added in one portion with vigorous stirring. After 1 h, TLC ($CHCl_3$/MeOH, 19:1 v/v) indicates complete reaction. The reaction mixture is concentrated on a rotary evaporator and diluted with dichloromethane to approximately 200 mL. After being washed with saturated $NaHCO_3$ (2×200 mL), the organic layer is dried with $Na_2SO_4$ and then concentrated in vacuo to an oil. Preparative silica gel chromatography with a gradient of MeOH in $CH_2Cl_2$ from 0 to 5% provides the desired product as a crystalline solid (3.3 g, 68%).

5'-O-Dimethoxytrityl-$N^2,N^6$-bis(phenoxyacetyl)-2,6-diaminopurine-2'-deoxyriboside-3'-O-(2-cyanoethyl-N,N'-diisoprolylphosphoramidite) (Compound 3).

A suspension of Compound 2 (3.1 g, 3.7 mmol) in a mixture of dichloromethane (30 mL) and diisopropylethylamine (4 mL) is treated with 2-cyanoethoxy N,N-diisopropylaminochlorophoshine (1.6 mL, 7.2 mmol). The reaction is stirred for 1 h, and quenched by addition of methanol (0.1 mL). After 2 min, dichloromethane (70 mL) is added and the solution is washed with 1M $NaHCO_3$ (100 mL) followed by saturated brine (100 mL). The organic layer is dried, filtered, and the solvent is removed in vacuo. The crude product is purified by preparative silica gel chromatography (ethyl acetate/dichloromethane/triethylamine, 45:45:5 v/v/v). After the purification the product is additionally precipitated in hexane to give a colorless solid (2.5 g, 65%)

N,N,N'-tris(9-fluorenylmethoxycarbonyl)-2,6-diaminopurine-2'-deoxyriboside (Compound 4, Reaction Scheme 2)

2,6-Diaminopurine-2'-deoxyriboside (2.3 g, 8.5 mmol) is dried by evaporation with dry pyridine and dissolved in 40 mL of the same solvent. Trimethylchlorosilane (5 mL, 3.9 mmol) is added dropwise to the ice cold solution and the reaction is kept for 1 min at 5° C. and 15 min at RT. 9-Fluorenylmethoxy carbonyl chloride (6.2 g, 24 mmol) is added, and the reaction mixture is stirred for 2 h. Hydrolysis of the trimethylsilyl groups and of excess chlorides is effected by addition of water (30 mL). After stirring for 18 h, the mixture is evaporated to near dryness and co-evaporated with toluene to remove residual pyridine. Upon addition of water (150 mL) a white solid is precipitated. The suspension is shaken with ether (100 mL) and is then filtered to give an off-white solid. TLC ($CHCl_3$/MeOH, 9:1 v/v) shows at least three new products. The major product with higher $R_f$ is isolated by silica gel chromatography using a gradient of methanol in dichloromethane. The product is a white solid (1.2 g, 15%).

5'-O-Dimethoxytrityl-N,N,N'-tris(9-fluorenylmethoxycarbonyl)-2,6-diaminopurine-21-deoxyriboside (Compound 5).

The title compound is prepared in accordance with the procedure described for the phenoxyacetylated analog in 70% yield.

5'-O-Dimethoxytrityl-N,N,N'-tris(9-fluorenylmethoxvcarbonyl)-2,6-diaminopurine-2'-deoxyriboside-3'-O-( 2-cyanoethyl-N,N'-diisopropylphosphoramidite) (compound 6).

The general method demonstrated described for the phenoxyacetylated analog Compound 3 (see above) is used to synthesize this phosphoramidite.

Preparation of hexanol-oxalyl Primer Support

This support is made by analogy to the literature method (Alul et al. Nucleic Acids Res. (1991) 19, 1527–1532). Solution I is prepared by dissolving of 2.8 g (6.7 mmol) of O-(4,4'-dimethoxytrityl)-1,6-hexanediol (5) in dry acetonitrile (8 mL). To prepare solution II, oxalyl chloride (0.6 mL) is added to a stirred solution of 1,2,4-triazole (2.1 g, 30 mmol) in 60 mL of acetonitrile, then pyridine (2 mL) is added to dissolve the resulting precipitate. Solution I is added dropwise to Solution II with stirring. After 1 h, amino modified Primer Support (20 g) (Pharmacia) is added in one portion. The suspension is swirled on a rotary shaker for 15 min, then filtered on a sintered glass filter, washed with methanol (200 mL), acetone (500 mL) and ether (200 mL). After being dried for 30 min in vacuo, the support is treated with a mixture of pyridine (60 mL), acetic anhydride (6 mL), and N-methyl imidazole (6 mL). After 15 min, the support is filtered, washed as described above, and dried in vacuo overnight. The product is analyzed for dimethoxytrityl content according to the literature method (Atkinson, T., and Smith, M., in "Oligonucleotide Synthesis, A Practical Approach", M. Gait, Ed., IRL Press, Washington, D. C. pp 35–81 (1984)), and in the specific example was found to have a loading of 32 $\mu$mol/g.

Oligonucleotide synthesis. Oligonucleotide synthesis is performed on a Pharmacia OligoPilot DNA synthesizer in 10 umol scale using either hexanol Primer Support which was prepared accordingly to the procedure described for hexanol CPG (Gamper et al.(1993) Nucleic Acids Res. 21, 145–150) or hexanoloxalyl Primer Support described above.

For the preparation of oligonucleotides containing 2-thiothymidine and 2-aminoadenosine, two alternative methods can be used. In the first method, N-phenoxyacetyl protected 5'-O-dimethoxytrityl-2'-deoxynucleside-2-cyanoethyl-N,N'-diisopropylamine-phosphoramidites are used. DNA synthesis cycle is carried out as for regular phosphoramidites. Time of the deprotection with concentrated ammonia is reduced to 2 h at 50° C. In the second method, Fmoc protected phosphoramidites are employed. The synthesis is performed using the hexanol-oxalyl Primer Support and the standard DNA synthesis cycle, with the exception of the capping step which is omitted. Deprotection is carried out by treatment of the solid support with 0.2M 1,8-diazobicyclo[5.4.0]undec-7-ene (DBU) in DMF for 5 min followed by 10% ammonia for additional 5 min.

What is claimed is:

1. A pair of oligonucleotides (ODNs), each of said ODNs comprising nucleotide moieties having naturally occurring aglycon bases and a combination of modified aglycon bases selected from the group consisting of the combinations (1) A', T', (2) G', C' and (3) A', T', G', C', the duplex form of said pair of ODNs having a melting temperature under physiological conditions of less than approximately 40° C., each of said pair of ODNs being substantially complementary in the Watson-Crick sense to one of the two strands of a duplexed target sequence in nucleic acid, wherein the nucleotide moieties having the modified bases have the following properties:

within complementary oligonucleotides A' does not form a stable hydrogen bonded base pair with T' and forms a stable hydrogen bonded base pair with T;

within complementary oligonucleotides T' does not form a stable hydrogen bonded base pair with A' and forms a stable hydrogen bonded base pair with A;

within complementary oligonucleotides G' does not form a stable hydrogen bonded base pair with C' and forms a stable hydrogen bonded base pair with C, and within complementary oligonucleotides C' does not form a stable hydrogen bonded base pair with GI and forms a stable hydrogen bonded base pair with G.

2. The ODNs of claim 1 wherein the nucleotide moiety A' has the structure selected from the groups shown by formulas (i), (ii) and (iii)

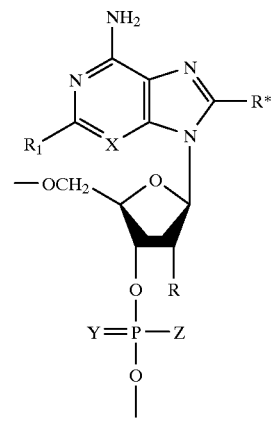

(i)

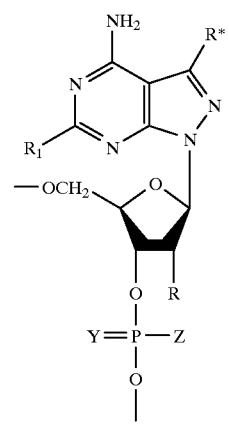

(ii)

-continued

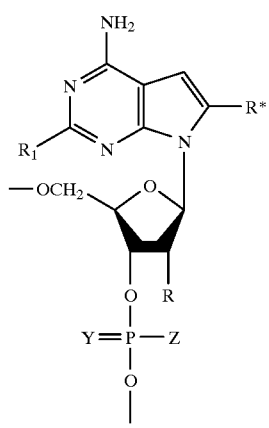
(iii)

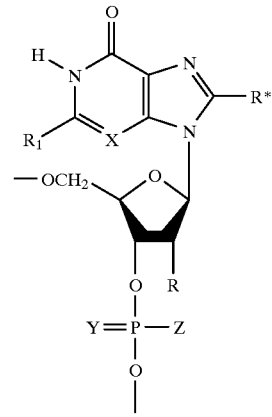
(v)

wherein

X is N or CH;

Y is O or S;

Z is OH or $CH_3$;

R is H, F, or $OR_2$, where $R_2$ is H, $C_{1-6}$ alkyl or allyl, and $R_1$ is $C_{1-4}$ alkyl, $C_{1-4}$ alkoxy, $C_{1-4}$ alkylthio, F, or $NHR_3$ where $R_3$ is H, or $C_{1-4}$ alkyl, and where R* is H, a cross-linking function or a reporter group.

3. The ODNs of claim 1 wherein the nucleotide moiety T' has the formula (iv)

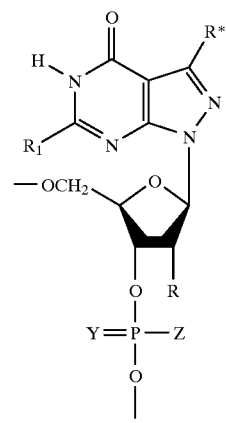
(vi)

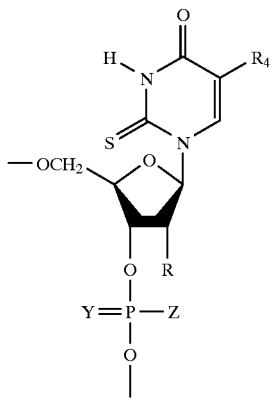
(iv)

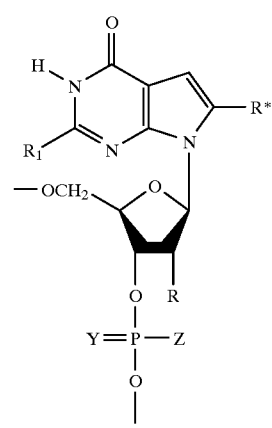
(vii)

wherein

Y is O or S;

Z is OH or $CH_3$;

R is H, F, or $OR_2$, where $R_2$ is H, $C_{1-6}$ alkyl or allyl, and $R_4$ is H, $C_{1-6}$ alkyl, $C_{1-6}$ alkenyl, $C_{1-6}$ alkynyl, a cross-linking function or a reporter group.

4. The ODNs of claim 1 wherein the nucleotide moiety G' has the structure selected from the groups shown by formulas (v), (vi) and (vii)

wherein

X is N or CH;

Y is O or S;

Z is OH or $CH_3$;

R is H, F, or $OR_2$, where $R_2$ is H, $C_{1-6}$ alkyl or allyl, and $R_1$ is H, $C_{1-4}$ alkyl, $C_{1-4}$ alkoxy, $C_{1-4}$ alkylthio, F, or $NHR_3$ where $R_3$ is H, or $C_{1-4}$ alkyl, and where R* is H, a cross-linking function or a reporter group.

5. The ODNs of claim 1 wherein the nucleotide C' has the structure selected from the groups shown by formulas (viii) and (ix)

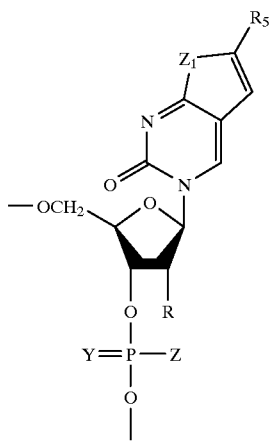

(viii)

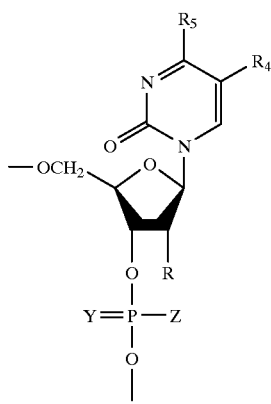

(ix)

wherein
Y is O or S;
Z is OH or CH$_3$;
R is H, F, or OR$_2$, where R$_2$ is H, C$_{1-6}$ alkyl or allyl, R$_4$ is H, C$_{1-6}$ alkyl, C$_{1-6}$ alkenyl, C$_{1-6}$ alknyl, a cross-linking function or a reporter group;
Z$_1$ is O or NH, and
R$_5$ is H, or C$_{1-4}$ alkyl.

6. The ODNs of claim 2 wherein the nucleotide moiety A' has the structure in accordance with formula (i).

7. The ODNs of claim 6 wherein X is N, Z is OH, and Y is O.

8. The ODNs of claim 7 wherein R$_1$ is NH$_2$.

9. The ODNs of claim 3 wherein Z is OH, and Y is O.

10. The ODNs of claim 9 wherein R$_4$ is CH$_3$.

11. The ODNs of claim 4 wherein the nucleotide moiety G' has the structure in accordance with formula (v).

12. The ODNs of claim 11 wherein X is N, Z is OH, and Y is O.

13. The ODNs of claim 12 wherein R$_1$ is H.

14. The ODNs of claim 5 wherein the nucleotide moiety C' has the structure in accordance with formula (viii).

15. The ODNs of claim 14 wherein, Z is OH, Z$_1$ is NH and Y is O.

16. The ODNs of claim 15 wherein R$_5$ is H.

17. The ODNs of claim 1 having approximately 5 to 99 nucleotide units.

18. The ODNs of claim 1 wherein each of the nucleotides is a 2'-deoxyribonucleotide.

19. The ODNs of claim 1 wherein each of the nucleotides is a ribonucleotide.

20. The ODNs of claim 1 comprising at least one nucleotide unit having a 2-O-methylribose moiety.

21. The ODNs of claim 1 comprising a cross-linking function covalently attached to at least one nucleotide unit.

22. The ODNs of claim 1 comprising a reporter group.

23. The ODNs of claim 1 wherein the combination of modified aglycon bases is A', T'.

24. The ODNs of claim 1 wherein the combination of modified aglycon bases is G', C'.

25. The ODNs of claim 1 wherein the combination of modified aglycon bases is A', T', G', C'.

26. The ODNs of claim 1 where the pair of oligonucleotides are linked to one another by a covalently bonded tether.

* * * * *

UNITED STATES PATENT AND TRADEMARK OFFICE
CERTIFICATE OF CORRECTION

Page 1 of 7

PATENT NO. : 5,912,340
DATED : June 15, 1999
INVENTOR(S) : Kutyavin et al.

It is certified that error appears in the above-identified patent and that said Letters Patent is hereby corrected as shown below:

Column 1, line 7, after "bases", delete "-".

Column 1, line 25, after "Troel", "." should be --,--.

Column 1, lines 55-6, "40° C." should be --40°C--.

Column 2, line 27, "40° C." should be --40°C--.

Column 4, line 45, "40° C." should be --40°C--.

Column 5, line 27, "ODNS" should be --ODNs--.

Column 5, line 61, after "applicable", insert --.--.

Column 6, Formula 6, next to $OCH_2$, insert -- - --.

Column 6, line 59, "BBC" should be --SBC--.

Column 9, line 47, "BBC" should be --SBC--.

Column 10, line 19, "So$_2$R''" should be --SO$_2$R''--.

Column 11, line 13, "BBC" should be --SBC--.

Column 11, Reaction Scheme 1, the two occurrence of "C=C" should be --C≡C--.

Column 12, line 42, "BBC" should be --SBC--.

Column 15, line 23, please underline the whole line.

Column 15, line 29, "hen" should be --when--.

UNITED STATES PATENT AND TRADEMARK OFFICE
CERTIFICATE OF CORRECTION

PATENT NO. : 5,912,340
DATED : June 15, 1999
INVENTOR(S) : Kutyavin et al.

It is certified that error appears in the above-identified patent and that said Letters Patent is hereby corrected as shown below:

Column 1, line 56, "ODNS" should be --ODNs--.

Column 4, line 41, "ODNS" should be --ODNs--.

Column 5, line 55, "cross-linkig" should be --cross-linking--.

Column 9, line 52, "-0-" should be -- -O- --.

Column 13, line 12, "crosslinking" should be --cross-linking--.

Column 13, line 51, "crosslinking" should be --cross-linking--.

Column 13, line 53, "crosslinking" should be --cross-linking--.

Column 13, line 59, "crosslinking" should be --cross-linking--.

Column 14, line 24, "crosslinking" should be --cross-linking--.

Column 14, line 59, "cross linking" should be --cross-linking--.

Column 14, line 66, "proceses" should be --processes--.

Column 15, line 34, "radiactive" should be --radioactive--.

Column 23, line 52, "Neverthless" should be --Nevertheless--.

Column 24, line 58, after "°C.", insert --)--.

Column 25, line 20, "ODNS" should be --ODNs--.

Column 25, line 47, after "solution", insert --was--.

Column 26, line 23, "an" should be --and--.

UNITED STATES PATENT AND TRADEMARK OFFICE
CERTIFICATE OF CORRECTION

PATENT NO. : 5,912,340
DATED : June 15, 1999
INVENTOR(S) : Kutyavin et al.

It is certified that error appears in the above-identified patent and that said Letters Patent is hereby corrected as shown below:

Column 15, line 43, "32P" should --$^{32}P$--.

Column 17, line 18, "BBC" should be --SBC--.

Column 17, line 23, "BBC" should be --SBC--.

Column 17, line 33, "BBC" should be --SBC--.

Column 18, line 9, "oligonucleotide" should be --Oligonucleotide--.

Column 23, Table 1, before the no. "75.6", insert --Sequence ID NO: 2--.

Column 23, Table 1, "Sequence ID NO: 7" should be --Sequence ID NO: 1--.

Column 23, Table 1, "Sequence ID NO. 8" should be --Sequence ID NO: 3--.

Column 23, Table 1, before the no. "20.2", insert --Sequence ID NO: 4--.

Column 24, Table 2, please delete all "." after "°C".

Column 26, line 57, after "5-amino-", "i" should be --1--.

Column 27, line 1, "80-90° C." should be --80-90°C--.

Column 28, line 26, "10x" should be --10X--.

Column 28, line 33, "10x" should be --10X--.

UNITED STATES PATENT AND TRADEMARK OFFICE
CERTIFICATE OF CORRECTION

PATENT NO. : 5,912,340
DATED : June 15, 1999
INVENTOR(S) : Kutyavin et al.

It is certified that error appears in the above-identified patent and that said Letters Patent is hereby corrected as shown below:

Column 28, line 36, "16° C." should be --16°C--.

COlumn 29, line 39, "benzylamine" should be --benzoylamine--.

Column 29, line 43, after "di-", "o" should be --O--.

Column 29, line 64, after "3", insert --,--.

Column 29, line 64, "benzylamine" should be --benzoylamine--.

Column 30, line 10, "deoxvuridine" should be --deoxyuridine--.

Column 30, line 15, "4-Phthalimidobut-1-yn" should be --4-Phthalimidobut-1-yne--.

Column 30, line 16, "60° C." should be --60°C--.

Column 30, line 25, "21" should be --2'--.

Column 30, line 62, "55° C." should be --55°C--.

Column 31, line 9, "oligonucleotides" should be --Oligonucleotides--.

Column 31, line 10, "-20° C." should be -- -20°C --.

Column 31, line 21, after "3", insert --,--.

Column 31, line 27, "40° C." should be --40°C--.

Column 31, line 32, "62° C." should be --62°C--.

UNITED STATES PATENT AND TRADEMARK OFFICE
CERTIFICATE OF CORRECTION

Page 5 of 7

PATENT NO. : 5,912,340
DATED : June 15, 1999
INVENTOR(S) : Kutyavin et al.

It is certified that error appears in the above-identified patent and that said Letters Patent is hereby corrected as shown below:

Column 31, line 32, "45° C." should be --45°C--.

Column 31, line 37, after "5", insert --,--.

Column 31, line 61, "160" should be --16°--.

Column 31, line 64, delete ",", and "Propynyl" should be --propynyl--.

Column 32, line 64, "diisopropylphosphoramidite" should be --diisopropylphosphoramidites--.

Column 33, line 41, "diisprolylphosphoramidite" should be --diisopropylphosphoramidite--.

Column 33, line 63, "5° C." should be --5°C--.

Column 34, line 11, "21" should be --2'--.

Column 34, line 17, "fluorenylmethoxvcarbonyl" should be --fluorenylmethoxycarbonyl--.

Column 34, line 49, "umol" should be --µmol--.

Column 39, line 30, "40° C." should be --40°C--.

Column 39, line 53, "GI" should be --G'--.

UNITED STATES PATENT AND TRADEMARK OFFICE
CERTIFICATE OF CORRECTION

PATENT NO. : 5,912,340
DATED : June 15, 1999
INVENTOR(S) : Kutyavin et al.

It is certified that error appears in the above-identified patent and that said Letters Patent is hereby corrected as shown below:

Column 26, line 44, after "solution", insert --was--.

Column 27, line 2, "dichloromthane" should be --dichloromethane--.

Column 27, line 25, after "stirred", insert --for--.

Column 31, line 52, "2-bromoethylammonlum" should be --2-bromoethylammonium--.

Column 32, line 2, after "60°", insert --C--.

Column 32, line 15, after "152", delete "0", and insert --°C--.

Column 32, line 28, after "110°", insert --C--.
Column 33, line 45, "diisopropylaminochlorophoshine" should be --diisopropylaminochlorophosphine--.

UNITED STATES PATENT AND TRADEMARK OFFICE
CERTIFICATE OF CORRECTION

PATENT NO. : 5,912,340
DATED : June 15, 1999
INVENTOR(S) : Kutyavin et al.

It is certified that error appears in the above-indentified patent and that said Letters Patent is hereby corrected as shown below:

Column 44, line 1, "alknyl" should be --alkynyl--.

Under Abstract, line 1, "ODNS" should be --ODNs--.

Under Abstract, line 16, "40° C." should be --40°C--.

Signed and Sealed this

Eighth Day of May, 2001

*Attest:*

NICHOLAS P. GODICI

*Attesting Officer*  Acting Director of the United States Patent and Trademark Office

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
       (A) LENGTH: 28 base pairs
       (B) TYPE: nucleic acid
       (C) STRANDEDNESS: single
       (D) TOPOLOGY: linear (ix) FEATURE:
       (A) NAME/KEY: misc_feature
       (B) LOCATION: 1..28
       (D) OTHER INFORMATION: /note= "corresponds to "Watson"
           strand of Hybrids I & III"

(xi) SEQUENCE DESCRIPTION: SEQ ID NO:1:

CTGACAACGA TCGGAGGACC GAAGGAGC                                    28

(2) INFORMATION FOR SEQ ID NO:2:

(i) SEQUENCE CHARACTERISTICS:
       (A) LENGTH: 28 base pairs
       (B) TYPE: nucleic acid
       (C) STRANDEDNESS: single
       (D) TOPOLOGY: linear (ix) FEATURE:
       (A) NAME/KEY: misc_feature
       (B) LOCATION: 1..28
       (D) OTHER INFORMATION: /note= "corresponds to "Crick"
           strand of Hybrids I & II"

(xi) SEQUENCE DESCRIPTION: SEQ ID NO:2:

GCTCCTTCGG TCCTCCGATC GTTGTCAG                                    28

(2) INFORMATION FOR SEQ ID NO:3:

(i) SEQUENCE CHARACTERISTICS:
       (A) LENGTH: 28 base pairs
       (B) TYPE: nucleic acid
       (C) STRANDEDNESS: single
       (D) TOPOLOGY: linear (ix) FEATURE:
       (A) NAME/KEY: modified_base
       (B) LOCATION: one-of(1, 5, 8, 12, 19, 20, 28)
       (D) OTHER INFORMATION: /mod_base= OTHER
           /note= "pyrrolo-[2,3-d]pyrimidine-2(3H)-one"

(ix) FEATURE:
       (A) NAME/KEY: modified_base
       (B) LOCATION: one-of(3, 9, 13, 14, 16, 17, 21, 24, 25, 27)
       (D) OTHER INFORMATION: /mod_base= OTHER
           /note= "hypoxanthine"

(ix) FEATURE:
       (A) NAME/KEY: misc_feature
       (B) LOCATION: 1..28
       (D) OTHER INFORMATION: /note= "corresponds to "Watson"
           strand of Hybrids II & IV"

(xi) SEQUENCE DESCRIPTION: SEQ ID NO:3:

NTNANAANNA TNNNANNANN NAANNANN                                    28

(2) INFORMATION FOR SEQ ID NO:4:

(i) SEQUENCE CHARACTERISTICS:

(A) LENGTH: 28 base pairs
            (B) TYPE: nucleic acid
            (C) STRANDEDNESS: single
            (D) TOPOLOGY: linear (ix) FEATURE:
            (A) NAME/KEY: modified_base
            (B) LOCATION: one-of(1, 9, 10, 17, 21, 24, 28)
            (D) OTHER INFORMATION: /mod_base= OTHER
                /note= "hypoxanthine"

(ix) FEATURE:
            (A) NAME/KEY: modified_base
            (B) LOCATION: one-of(2, 4, 5, 8, 12, 13, 15, 16, 20, 26)
            (D) OTHER INFORMATION: /mod_base= OTHER
                /note= "pyrrolo-[2,3-d]pyrimidine-2(3H)-one"

(ix) FEATURE:
            (A) NAME/KEY: misc_feature
            (B) LOCATION: 1..28
            (D) OTHER INFORMATION: /note= "corresponds to "Crick"
                strand of Hybrids III & IV"

(xi) SEQUENCE DESCRIPTION: SEQ ID NO:4:

NNTNNTTNNN TNNTNNNATN NTTNTNAN                                              28

(2) INFORMATION FOR SEQ ID NO:5:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:5:

GTAAGAGAAT TATGCAGTGC                                                       20

(2) INFORMATION FOR SEQ ID NO:6:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:6:

GCACTGCATA ATTCTCTTAC                                                       20

(2) INFORMATION FOR SEQ ID NO:7:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ix) FEATURE:
            (A) NAME/KEY: modified_base
            (B) LOCATION: one-of(2, 10, 11, 13, 18)
            (D) OTHER INFORMATION: /mod_base= OTHER
                /note= "d2sThymine replaces all dThymine"

(ix) FEATURE:
            (A) NAME/KEY: modified_base
            (B) LOCATION: one-of(3, 4, 6, 8, 9, 12, 16)
            (D) OTHER INFORMATION: /mod_base= OTHER
                /note= "d2amAdenine replaces all dAdenine"

(xi) SEQUENCE DESCRIPTION: SEQ ID NO:7:

GTAAGAGAAT TATGCAGTGC                                                       20

(2) INFORMATION FOR SEQ ID NO:8:

```
    (i) SEQUENCE CHARACTERISTICS:
        (A) LENGTH: 20 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: one-of(3, 8, 10, 11, 19)
        (D) OTHER INFORMATION: /mod_base= OTHER
            /note= "d2amAdenine replaces all dAdenine"

(ix) FEATURE:
        (A) NAME/KEY: modified_base
        (B) LOCATION: one-of(5, 9, 12, 13, 15, 17, 18)
        (D) OTHER INFORMATION: /mod_base= OTHER
            /note= "d2sThymine replaces all dThymine"

(xi) SEQUENCE DESCRIPTION: SEQ ID NO:8:

GCACTGCATA ATTCTCTTAC                                              20
```